(12) United States Patent
Targoff et al.

(10) Patent No.: US 6,610,823 B1
(45) Date of Patent: Aug. 26, 2003

(54) ANTIGENS ASSOCIATED WITH POLYMYOSITIS AND WITH DERMATOMYOSITIS

(75) Inventors: Ira N. Targoff, Oklahoma City, OK (US); Qun Ge, Oklahoma City, OK (US)

(73) Assignees: Board of Regents of the University of Oklahoma, Norman, OK (US); Oklahoma Medical Research Foundation, Oklahoma City, OK (US)

( * ) Notice: Subject to any disclaimer, the term of this patent is extended or adjusted under 35 U.S.C. 154(b) by 0 days.

(21) Appl. No.: 07/945,295

(22) Filed: Sep. 9, 1992

Related U.S. Application Data

(63) Continuation-in-part of application No. 07/579,023, filed on Sep. 7, 1990, now abandoned.

(51) Int. Cl.$^7$ .......................... A61K 38/00; C07K 16/00
(52) U.S. Cl. ...................................... 530/324; 530/387.9
(58) Field of Search ............................. 435/69.1, 270.1; 530/350, 324, 387.1, 391.1; 536/23.1, 24.3, 24.31, 23.5

(56) References Cited

PUBLICATIONS

Targoff and Reichlin, "The Association between Mi–2 antibodies and Dermatomyositis," Arthritis and Rheumatism, vol. 28, No. 7, Jul. 1985, pp. 796–803.*

Ge, et al., The Journal of Clinical Investigation, Inc., vol. 90, pp. 559–570, Aug. 1992.*

Targoff et al., Arthritis and Rheumatism, vol. 28, No. 7, 1985, pp. 796–803.*

Alderuccio, "Molecular Characterization of an Autoantigen of PM–Scl in the Polymyositis/Scleroderma Overlap Syndrome: A Unique and Complete Human cDNA Encoding an Apparent 75–kD Acidic Protein of the Nucleolar Complex," The Journal of Experimental Medicine, 173:941–952 ((1991).

Blaszczyk, M., et al., "Autoantibodies to Nucleolar Antigens in Systemic Scleroderma: Clinical Correlations," British Journal of Dermatology, 123:421–430 (1990).

Blaszczyk, M., et al., "Childhood Scleromyositis: An Overlap Syndrome Associated with PM–Scl Antibody," Pediatric Dermatology, 8(1):1–8 (Mar. 1991).

M. Blüthner, E. Genth and F. Bautz, "Cloning of a cDNA–Fragment Coding for an Epitope Recognized by Anti–PM/Scl–Autoantibodies," Abstract from the First International Workshop on the Molecular and Cell Biology of Autoantibodies and Autoimmunity, Heidelberg, Federal Republic of Germany, (Springer–Verlag Jul. 27–29, 1989).

Bradford, M.M., "A Rapid and Sensitive method for the Quantitation of Microgram Quantities of Protein Utilizing the Principle of Protein–Dye Binding," Analytical Biochemistry, 72:248–254 (1976).

Brendel, et al., "Very long charge runs in systemic lupus erythematosus–associated autoantigens," Proceedings of the National Academy of Sciences, 88(3):1536–1540 (Feb. 1, 1991).

Devereux, J., et al., "A Comprehensive Set of Sequence Analysis Programs for the VAS," Nucleic Acids Research, 12(1):386–395 (1984).

Frohman, M.A., et al., "Rapid Production of Full–length cDNAs from Rare Transcripts: Amplification Using a Single Gene–specific Oligonucleotide Primer," Proc. Natl. Acad. Sci. USA, 85:8998–9002 (1988).

Ge, Targott, et al., "Analysis of Full–Length Sequence of the 100 kD Protein of the PM–SCL Antigen," Abstracts of Scientific Presentations, 34(9):S134 (Sep. 1991).

Ge, Targoff, et al., "Molecular Cloning of an Antigenic Component of the PM–SCL Antigen," Abstracts of Scientific Presentations, 33(9): (Sep. 1990).

Gelpi, C., et al., "Identification of Protein Components Reactive with Anti–PM/Scl Autoantibodies," Clin. exp. Immunol. 81:59–64 (1990).

Genth, E., et al., "Immunogenetic Associations of Scleroderma–related Antinuclear Antibodies," Arthritis and Rheumatism, 33(5):657–665 (1990).

Hirakata, et al., "Autoantibodies to Small Nuclear and Cytoplasmic Ribonucleoproteins in Japanese Patients with Inflammatory Muscle Disease," Official Journal of the American College of Rheumatology, 35(4):449–456 (Apr. 1992).

Itoh, et al., "Protein Heterogeneity in the Human Ro/SSA Ribonucleoproteins," The Journal of Clinical Investigation, 87(1):177–186 (Jan. 1991).

Laemmli, U.K., "Cleavage of Structural Proteins During the Assembly of the Head of Bacteriophage T4," Nature, 227:680–685 (1970).

Leff, et al., "Distinct Seasonal Patterns in the Onset of Adult Idiopathic Inflammatory Myopathy in Patients with Anti–Jo–1 and Anti–Signal Recognition Particle Autoantibodies," Official Journal of the American College of Rheumatology, 34(7–12):1391–1396 (1991).

Loh, E.Y., et al., "Polymerase Chain Reaction with Single- –Sided Specificity: Analysis of T Cell Receptor δ Chain," Science, 243:217–220 (1989).

Love, et al., "A New Approach to the Classification of Idiopathic Inflammatory Myopathy: Myositis–Specific Autoantibodies Define Useful Homogeneous Patient Groups," Medicine, 70(6):360–374 (1991).

(List continued on next page.)

Primary Examiner—Bradley L. Sisson
(74) Attorney, Agent, or Firm—Holland & Knight LLP

(57) ABSTRACT

Isolated DNA molecules encoding at least one epitope of the Mi-2 antigen and at least one epitope of the PM-Scl antigen are provided. The DNA may be used as probes to obtain related DNA. Proteins expressed from the DNA may be used in assays for the diagnosis of dermatomyositis and polymyositis, particularly polymyositis-scleroderma overlap disorders. The expressed proteins may also be used for purification of the associated autoantigens.

6 Claims, 4 Drawing Sheets

OTHER PUBLICATIONS

F. Miller, S. Twitty, T. Biswas and P. Plotz, "Origin and Regulation of a Disease–Specific Autoantibody Response: Antigenic Epitopes, Spectrotype Stability, and Isotype Restriction of Anti–Jo–1 Autoantibodies," *The Journal of Clinical Investigation 85:* 468–475 (Feb. 1990).

Mimori, T., "Scleroderma–Polymyositis Overlap Syndrome," *International Journal of Dermatology,* 26(7):419–425 (1987).

Nilasena, D.S., et al., "Molecular Cloning of the Dermatomyositis (DM)–Associated Mi–2 Antigen," *Official Journal of the American College of Rheumatology,* 33(9) (1990).

Nilasena, D.S., et al., "Biochemical Analysis of the Dermatomyositis Autoantigen MI2," *1990 ASBMB/AAI Abstract Form.*

M. Nishikai and M. Reichlin, "Heterogeneity of Precipitating Antibodies in Polymyositis and Dermatomyositis," *Arthritis and Rheumatism 23*(8): 881–888 (Aug. 1980).

M. Nishikai and M. Reichlin, "Purification and Characterization of a Nuclear Non–Histone Basic Protein (Mi–1) which Reacts with Anti–Immunoglobulin Sera and the Sera of Patients with Dermatomyositis," *Molecular Immunology 17:* 1129–1141 (1980).

Oddis, C.V., et al., "The Association of HLA Class II Alleles with Autoantibody to PM–SCL," *American College of Rheumatology,* 34(5) (1991).

Plotz, P.H., et al., "Current Concepts in the Idiopathic Inflammatory Myopathies: Polymyositis, Dermatomyositis, and Related Disorders," *Annals of Internal Medicine,* 111(2):143–157 (1989).

Pollard, K.M., et al., "Autoantibodies in Scleroderma," *Clinical and Experimental Rheumatology,* 7/S–3:57–62 (1989).

M. Reichlin and F. Arnett, "Multiplicity of Antibodies in Myositis Sera," *Arthritis and Rheumatism 27*(10): 1150–1156 (Oct. 1984).

M. Reichlin, I. Targoff, et al., "Antibodies to a Nuclear/Nucleolar Antigen in Patients with Polymyositis Overlap Syndromes," *Journal of Clinical Immunology 4*(1): 40–44 (1984).

M. Reichlin and M. Mattioli, "Description of a Serological Reaction Characteristic of Polymyositis," *Clinical Immunology and Immunopathology 5:* 12–20 (1976).

G. Reimer, U. Scheer, J. Peters, and E. Tan, "Immunolocalization and Partial Characterization of a Nucleolar Autoantigen (PM–Sc1) Associated with Polymyositis/Scleroderma Overlap Syndromes," *Journal of Immunology 137*(12): 3802–3808 (Dec. 15, 1986).

G. Reimer, V. Steen, et al., "Correlates Between Autoantibodies to Nucleolar Antigens and Clinical Features in Patients with Systemic Sclerosis (Scleroderma)," *Arthritis and Rheumatism 31*(4): 525–532 (Apr. 1988).

Sanger, F., et al., "DNA Sequencing with Chain–terminating Inhibitors," *Biochemistry,* 72(12):5463–5467 (1977).

Tabor, S., et al., "DNA Sequence Analysis with a Modified Bacteriophage T7 DNA Polymerase," *Proc. Natl. Acad. Sci. USA, Biochemistry,* 84:4767–4771 (1987).

E. Tan, "Antinuclear Antibodies: Diagnostic Markers for Autoimmune Diseases and Probes for Cell Biology," *Advances in Immunology 44:* 93–151 (Academic Press, New York 1989).

I. Targoff, "Autoantibodies to Aminoacyl–Transfer RNA Synthetases for Isoleucine and Glycine: Two Additional Synthetases are Antigenic in Myositis," *The Journal of Immunology 144*(5): 1737–1743 (Mar. 1, 1990).

I. Targoff, "Autoantibodies in Polymyositis," *Rheumatic Disease Clinics of North America,* 18(2):455–483 (May 1992).

Targoff, I.N., et al., "Clinical Features and Immunologic Testing of Patients with Anti–MI–2 Antibodies," *Arthritis and Rheumatis.* 33(7–12):S72 (1990).

Targoff, I.N., "Dermatomyositis and Polymyositis," *Curr. Probl. Dermatol.,* 134–180 (1991).

Targoff, I.N., "Immune Mechanisms in Myositis," *Current Science ISSN 1040–8711,* 882–888 (1990).

Targoff, I.N., "Immunologic Aspects of Myositis," *Current Opinion in Rheumatology 1:* 432–442 (1989).

Targoff, I.N., "Inflammatory Muscle Disease," *The Lung in Rheumatic Diseases,* 303–328 (1990).

Targoff, I.N., "Laboratory Manifestations of Polymyositis/Dermatomyositis," *Laboratory Manifestations,* 6(2): 76–92 (1988).

Targoff, I.N., "Polymyositis," *Systemic Autoimmunity,* 201–247 (1991).

I. Targoff, G. Raghu and M. Reichlin, "Antibodies to Mi–1 in SLE; Relationship to Other Precipitins and Reaction with Bovine Immunoglobulin," *Clinical Experimental Immunology 53:* 76–82 (1983).

I. Targoff and M. Reichlin, "The Association Between Mi–2 Antibodies and Dermatomyositis," *Arthritis and Rheumatism 28*(7): 796–803 (Jul. 1985).

I. Targoff and M. Reichlin, "Humoral Immunity in Polymyositis and Dermatomyositis," *The Mount Sinai Journal of Medicine 55*(6): 487–493 (Nov. 1988).

Targoff and M. Reichlin, "Immunological Aspects," *Inflammatory Diseases of Muscle,* 37–70 (1988).

I. Targoff and M. Reichlin, "Measurement of Antibody to Jo–1 by ELISA and Comparison to Enzyme Inhibitory Activity," *The Journal of Immunology 138*(9): 2874–2882 (May 1, 1987).

I. Targoff and M. Reichlin, "Nucleolar Localization of the PM–Scl Antigen," *Arthritis and Rheumatism 28*(2): 226–230 (Feb. 1985).

Towbin, H., et al., "Electrophoretic Transfer of Proteins from Polyacrylamide Gels to Nitrocellulose Sheet: Procedure and Some Applications," *Proc. Natl. Acad. Sci. USA,* 76(9):4350–4354 (1979).

E. Treadwell, M. Alspaugh, J. Wolfe, and G. Sharp, "Clinical Relevance of PM–1 Antibody and Physiochemical Characterization of PM–1 Antigen," *The Journal of Rheumatology 11*(5): 658–662 (1984).

J. Wolfe, E. Adelstein and G. Sharp, "Antinuclear Antibody with Distinct Specificity for Polymyositis," *Journal of Clinical Investigation 59:* 176–178 (Jan. 1977).

\* cited by examiner

RESTRICTION ENZYME MAP OF THE INSERT OF CLONE JH2 CODING
FOR A PORTION OF THE PM-SCL PROTEIN

```
0          0.5         1.0         1.5         2.0         2.5
─────────────────────────────────────────────────────────────────
      a         b   c    d e            f    g    h
```

Numbers indicate points along cDNA strand.
Letters indicate restriction enzyme digestion sites.

Taq I cleaves at a and b.

Xho I cleaves at c.

Sma I cleaves at d and g.

Pst I cleaves at e and h.

Kpn I cleaves at f.

Fragments were derived from double digestions with either TaqI + KpnI (Fragments I, II, III, and IV) or XhoI and PstI (fragments V, VI, VII, and VIII).

```
                        Approx size
0 to a = fragment I.    350 bp
a to b = fragment II.   450 bp
b to f = fragment III.  950 bp
f to 2.5 = fragment IV. 750 bp 0 to c = fragment V.    900 bp
c to e = fragment VI.   325 bp
e to h = fragment VII.  825 bp
h to 2.5 = fragment VIII. 450 bp
```

*FIG. 1*

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 1053 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (vi) ORIGINAL SOURCE:
      (A) ORGANISM: Homo sapiens
      (F) TISSUE TYPE: Blood (vii) IMMEDIATE SOURCE:
      (A) LIBRARY: Human thymocyte lambda gt11
      (B) CLONE: L1

(xi) SEQUENCE DESCRIPTION: SEQ ID NO:1:

GAATTCCGGC TAGGGCTTCT GGGTGGCAAG AGGAAGAAAG GAGGCTCGAG CGACGAAGGT    60

-continued

```
CCTGAACCAG AGGCTGAGGA ATCAGACCTG GACAGTGGCA GTGTCCACAG TGCCTCAGGC      120

CGGCCTGATG GCCCTGTCCG CACCAAGAAA CTAAAGAGAG GCCGGCCAGG AAGGAAGAAG      180

AAGAAGGTCC TGGGCTGTCC TGCAGTGGCC GGGGAGGAGG AGGTTGATGG CTACGAGACG      240

GATCACCAGG ATTACTGTGA GGTGTGCCAG CAGGGTGGGG AAATTATTCT GTGTGACACC      300

TGCCCTCGTG CCTACCACCT CGTCTGCCTT GATCCTGAGC TTGACCGGGC TCCAGAGGGC      360

AAATGGAGCT GCCCTCACTG TGAGAAGGAG GGGGTCCAGT GGGAGGCCAA GGAGGAAGAA      420

GAAGAATACG AAGAGGAGGG AGAGGAAGAA GGGGAGAAGG AGGAGGAGGA TGATCACATG      480

GAGTACTGCC GCGTATGCAA GGACGGCGGG GAGCTCCTGT GCTGTGACGC GTGCATCTCC      540

TCCTACCACA TTCATTGTCT AAACCCTCCC CTGCCTGACA TTCCCAATGG TGAATGGCTG      600

TGTCCCCGAT GCACATGCCC CGTGCTGAAG GGTCGAGTGC AGAAGATCCT ACATTGGCGG      660

TGGGGGGAGC CACCTGTAGC AGTGCCAGCC CCTCAACAGG CAGATGGAAA TCCAGATGTC      720

CCACCCCCCC GTCCTCTTCA AGGCAGATCA GAGCGAGAGT TCTTTGTCAA GTGGGTAGGA      780

CTATCCTACT GGCACTGCTC CTGGGCCAAG GAGCTTCAGC TGGAAATCTT CCATTTGGTT      840

ATGTATCGAA ACTACCAGCG GAAGAATGAC ATGGATGAGC CCCCACCCCT GGACTATGGC      900

TCCGGCGAGG ATGATGGGAA GAGCGACAAG CGTAAAGTGA AGACCCGCA CTATGCTGAG      960

ATGGAGGAGA AGTACTATCG TTTTGGCATC AAGCCAGAGT GGATGACCGT CCACCGCATC     1020

ATCAACCACA GTGTGGATAA AAAGGCCGGA ATT                                  1053
```

(2) INFORMATION FOR SEQ ID NO:2:

(i) SEQUENCE CHARACTERISTICS:
        (A) LENGTH: 351 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
        (A) ORGANISM: Homo sapiens
        (F) TISSUE TYPE: Blood (vii) IMMEDIATE SOURCE:
        (A) LIBRARY: Human thymocyte lambda gt11
        (B) CLONE: L1

(xi) SEQUENCE DESCRIPTION: SEQ ID NO:2:

```
Glu Phe Arg Leu Gly Leu Leu Gly Gly Lys Arg Lys Lys Gly Ser
1               5                   10                  15

Ser Asp Glu Gly Pro Glu Pro Glu Ala Glu Glu Ser Asp Leu Asp Ser
                20                  25                  30

Gly Ser Val His Ser Ala Ser Gly Arg Pro Asp Gly Pro Val Arg Thr
            35                  40                  45

Lys Lys Leu Lys Arg Gly Arg Pro Gly Arg Lys Lys Lys Val Leu
50                  55                  60

Gly Cys Pro Ala Val Ala Gly Glu Glu Glu Val Asp Gly Tyr Glu Thr
65                  70                  75                  80

Asp His Gln Asp Tyr Cys Glu Val Cys Gln Gln Gly Gly Glu Ile Ile
                85                  90                  95
```

```
Leu Cys Asp Thr Cys Pro Arg Ala Tyr His Leu Val Cys Leu Asp Pro
            100                 105                 110

Glu Leu Asp Arg Ala Pro Glu Gly Lys Trp Ser Cys Pro His Cys Glu
        115                 120                 125

Lys Glu Gly Val Gln Trp Glu Ala Lys Glu Glu Glu Glu Tyr Glu
    130                 135                 140

Glu Glu Gly Glu Glu Gly Glu Lys Glu Glu Asp Asp His Met
145                 150                 155                 160

Glu Tyr Cys Arg Val Cys Lys Asp Gly Gly Glu Leu Leu Cys Cys Asp
                165                 170                 175

Ala Cys Ile Ser Ser Tyr His Ile His Cys Leu Asn Pro Pro Leu Pro
            180                 185                 190

Asp Ile Pro Asn Gly Glu Trp Leu Cys Pro Arg Cys Thr Cys Pro Val
        195                 200                 205

Leu Lys Gly Arg Val Gln Lys Ile Leu His Trp Arg Trp Gly Glu Pro
    210                 215                 220

Pro Val Ala Val Pro Ala Pro Gln Gln Ala Asp Gly Asn Pro Asp Val
225                 230                 235                 240

Pro Pro Pro Arg Pro Leu Gln Gly Arg Ser Glu Arg Glu Phe Phe Val
                245                 250                 255

Lys Trp Val Gly Leu Ser Tyr Trp His Cys Ser Trp Ala Lys Glu Leu
            260                 265                 270

Gln Leu Glu Ile Phe His Leu Val Met Tyr Arg Asn Tyr Gln Arg Lys
        275                 280                 285

Asn Asp Met Asp Glu Pro Pro Pro Leu Asp Tyr Gly Ser Gly Glu Asp
    290                 295                 300

Asp Gly Lys Ser Asp Lys Arg Lys Val Lys Asp Pro His Tyr Ala Glu
305                 310                 315                 320

Met Glu Glu Lys Tyr Tyr Arg Phe Gly Ile Lys Pro Glu Trp Met Thr
                325                 330                 335

Val His Arg Ile Ile Asn His Ser Val Asp Lys Lys Ala Gly Ile
            340                 345                 350

(2) INFORMATION FOR SEQ ID NO:3:

(i) SEQUENCE CHARACTERISTICS:
        (A) LENGTH: 2739 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Homo sapiens
        (F) TISSUE TYPE: Blood (vii) IMMEDIATE SOURCE:
        (A) LIBRARY: Human thyocyte lambda gt11
        (B) CLONE: JH4B1

(xi) SEQUENCE DESCRIPTION: SEQ ID NO:3:

GACAAGCTCT CGCGAGACGA GCCGTGCAGG CTGAAAAAAT GGCGCCACCC AGTACCCGGG      60

AGCCCAGGGT CCTGTCGGCG ACCAGCGCAA CCAAATCCGA CGGAGAGATG GTGCTGCCAG     120

GCTTCCCGGA CGCCGACAGC TTTGTGAAGT TTGCTCTTGG GTCCGTGGTG GCAGTCACCA     180
```

-continued

```
AGGCATCTGG GGGCCTACCA CAGTTTGGCG ATGAGTATGA TTTTTACCGA AGTTTTCCTG      240
GCTTCCAAGC ATTTTGCGAA ACACAGGGAG ACAGGTTGCT TCAGTGCATG AGCAGAGTAA      300
TGCAGTACCA TGGGTGTCGC AGCAACATTA AGGATCGAAG TAAAGTGACT GAGCTGGAAG      360
ACAAGTTTGA TTTACTAGTT GATGCCAATG ATGTAATTCT GGAGAGAGTG GGTATTTTAC      420
TGGATGAAGC CTCAGGTGTA ACAAGAATC AACAGCCTGT CCTCCCTGCC GGCTTGCAGG       480
TCCCCAAAAC GGTAGTGTCC AGCTGGAACC GTAAGGCAGC AGAATATGGC AAAAAAGCAA      540
AATCTGAAAC TTTCCGGCTG CTTCATGCAA AAAATATCAT CCGACCTCAG CTCAAGTTTC      600
GAGAGAAGAT TGACAATTCC AACACACCAT TTCTTCCTAA AATCTTCATC AAACCCAATG      660
CTCAGAAACC TCTCCCTCAA GCTCTCTCTA AGGAAAGGCG GGAACGCCCA CAGGATCGTC      720
CTGAGGACTT GGACGTCCCC CCTGCACTGG CTGATTTCAT CCATCAGCAG AGAACCCAGC      780
AGGTTGAGCA AGACATGTTT GCACATCCTT ATCAATATGA ACTAAATCAC TTTACCCCAG      840
CAGATGCAGT GCTTCAAAAG CCACAACCCC AGTTATACAG ACCTATAGAA GAGACACCAT      900
GCCATTTCAT ATCCTCCCTG GATGAACTCG TGGAACTCAA CGAAAAGCTC TTGAATTGTC      960
AGGAATTTGC AGTTGACTTG GAGCACCACT CTTACAGGAG CTTCCTGGGA CTGACCTGCC     1020
TGATGCAAAT TTCTACTCGG ACGGAAGACT TCATCATTGA CACCCTCGAG CTTCGAAGTG     1080
ACATGTACAT TCTCAATGAG AGCCTCACAG ACCCAGCCAT CGTTAAGGTC TTTCATGGTG     1140
CTGATTCAGA CATAGAATGG CTACAGAAAG ACTTTGGGTT GTATGTAGTA ACATGTTTG      1200
ATACTCATCA GGCAGCACGC CTTCTTAACC TGGGCAGGCA CTCACTCGAT CATCTCCTGA     1260
AACTCTACTG CAACGTGGAC TCAAACAAGC AATATATCAGCT GGCTGATTGG AGAATACGCC    1320
CTCTGCCCGA GGAGATGCTC AGCTACGCCC GGGATGACAC CCATTACCTG CTATATATCT     1380
ATGACAAAAT GAGGCTGGAG ATGTGGGAGC GCGGCAACGG GCAGCCCGTG CAGCTGCAGG     1440
TGGTGTGGCA ACGGAGCAGG GACATCTGCC TCAAGAAATT CATCAAACCT ATCTTCACGG     1500
ATGAGTCCTA CCTTGAACTC TATAGGAAGC AGAAGAAGCA CCTTAACACA CAGCAGTTGA     1560
CAGCCTTTCA GCTGCTGTTT GCCTGGAGGG ATAAAACAGC TCGCAGGGAA GATGAAAGTT     1620
ACGGATATGT ACTGCCAAAC CACATGATGC TGAAAATAGC TGAAGAACTG CCTAAGGAAC     1680
CTCAGGGCAT CATAGCTTGC TGCAACCCAG TACCGCCCCT TGTGCGGCAG CAGATCAACG     1740
AAATGCACCT TTTAATCCAG CAGGCCCGAG AGATGCCCCT GCTCAAGTCT GAAGTTGCAG     1800
CCGGAGTGAA GAAGAGCGGA CCGCTGCCCA GTGCTGAGAG ATTGGAGAAT GTTCTCTTTG     1860
GACCTCACGA CTGCTCCCAT GCCCCTCCGG ATGGCTATCC AATCATCCCA ACCAGTGGAT     1920
CTGTGCCAGT TCAGAAGCAG GCGAGCCTCT TCCCTGATGA AAAAGAAGAT AACTTGCTGG     1980
GTACCACATG CCTGATTGCC ACAGCTGTCA TCACGTTATT TAATGAACCT AGTGCTGAAG     2040
ACAGTAAAAA GGGTCCATTG ACAGTTGCAC AGAAAAAAGC CCAGAACATC ATGGAGTCCT     2100
TTGAAAATCC ATTTAGGATG ATCAGCAACC GTTGGAAGCT GGCCCAGGTA CAAGTACAAA     2160
AAGAGACTAA AGAAGCTGTC AAGAAGAAGG CAGCTGAGCA AACAGCTGCC CGGGAACAGG     2220
CAAAGGAGGC GTGCAAAGCT GCAGCAGAAC AGGCCATCTC CGTCCGACAG CAGGTCGTGC     2280
TAGAAAATGC TGCAAAGAAG AGAGAGCGAG CAACAAGCGA CCCAAGGACC ACAGAACAGA     2340
AACAAGAGAA GAAACGACTC AAAATTTCCA AGAAGCCAAA GGACCCAGAG CCACCAGAAA     2400
AGAGTTTAC GCCTTACGAC TACAGCCAGT CAGACTTCAA GGCTTTTGCT GGAAACAGCA     2460
AATCCAAAGT TTCTTCTCAG TTTGATCCAA ATAAACAGAC CCCGTCTGGC AAGAAATGCA     2520
```

```
TTGCAGCCAA AAAAATTAAA CAGTCGGTGG GAAACAAAAG CATGTCCTTT CCAACTGGAA      2580

AGTCAGACAG AGGCTTCAGG TACAACTGGC CACAGAGATA GTCCTGGAAG ACACGTGGCG      2640

CCTGTGGACC GGAAGCACCA AATGCTGGTG CTGCTTTTGT ACATACATAT TTTTAAACCA      2700

TTAAAATTCT TCCTGAAGAA AAAAAAAAAA AAAAAAAA                             2739
```

(2) INFORMATION FOR SEQ ID NO:4:

(i) SEQUENCE CHARACTERISTICS:
        (A) LENGTH: 860 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (vi) ORIGINAL SOURCE:
        (A) ORGANISM: Homo sapiens
        (F) TISSUE TYPE: Blood (vii) IMMEDIATE SOURCE:
        (A) LIBRARY: Human thymocyte lambda gt11
        (B) CLONE: JH4B1

(xi) SEQUENCE DESCRIPTION: SEQ ID NO:4:

```
Met Ala Pro Pro Ser Thr Arg Glu Pro Arg Val Leu Ser Ala Thr Ser
 1               5                  10                  15

Ala Thr Lys Ser Asp Gly Glu Met Val Leu Pro Gly Phe Pro Asp Ala
                20                  25                  30

Asp Ser Phe Val Lys Phe Ala Leu Gly Ser Val Val Ala Val Thr Lys
            35                  40                  45

Ala Ser Gly Gly Leu Pro Gln Phe Gly Asp Glu Tyr Asp Phe Tyr Arg
        50                  55                  60

Ser Phe Pro Gly Phe Gln Ala Phe Cys Glu Thr Gln Gly Asp Arg Leu
65                  70                  75                  80

Leu Gln Cys Met Ser Arg Val Met Gln Tyr His Gly Cys Arg Ser Asn
                85                  90                  95

Ile Lys Asp Arg Ser Lys Val Thr Glu Leu Glu Asp Lys Phe Asp Leu
               100                 105                 110

Leu Val Asp Ala Asn Asp Val Ile Leu Glu Arg Val Gly Ile Leu Leu
            115                 120                 125

Asp Glu Ala Ser Gly Val Asn Lys Asn Gln Gln Pro Val Leu Pro Ala
        130                 135                 140

Gly Leu Gln Val Pro Lys Thr Val Val Ser Ser Trp Asn Arg Lys Ala
145                 150                 155                 160

Ala Glu Tyr Gly Lys Lys Ala Lys Ser Glu Thr Phe Arg Leu Leu His
                165                 170                 175

Ala Lys Asn Ile Ile Arg Pro Gln Leu Lys Phe Arg Glu Lys Ile Asp
               180                 185                 190

Asn Ser Asn Thr Pro Phe Leu Pro Lys Ile Phe Ile Lys Pro Asn Ala
            195                 200                 205

Gln Lys Pro Leu Pro Gln Ala Leu Ser Lys Glu Arg Arg Glu Arg Pro
        210                 215                 220

Gln Asp Arg Pro Glu Asp Leu Asp Val Pro Pro Ala Leu Ala Asp Phe
225                 230                 235                 240

Ile His Gln Gln Arg Thr Gln Gln Val Glu Gln Asp Met Phe Ala His
```

```
                    245                 250                 255
Pro Tyr Gln Tyr Glu Leu Asn His Phe Thr Pro Ala Asp Ala Val Leu
                260                 265                 270

Gln Lys Pro Gln Pro Gln Leu Tyr Arg Pro Ile Glu Glu Thr Pro Cys
        275                 280                 285

His Phe Ile Ser Ser Leu Asp Glu Leu Val Glu Leu Asn Glu Lys Leu
        290                 295                 300

Leu Asn Cys Gln Glu Phe Ala Val Asp Leu Glu His Ser Tyr Arg
305                 310                 315                 320

Ser Phe Leu Gly Leu Thr Cys Leu Met Gln Ile Ser Thr Arg Thr Glu
                325                 330                 335

Asp Phe Ile Ile Asp Thr Leu Glu Leu Arg Ser Asp Met Tyr Ile Leu
                340                 345                 350

Asn Glu Ser Leu Thr Asp Pro Ala Ile Val Lys Val Phe His Gly Ala
                355                 360                 365

Asp Ser Asp Ile Glu Trp Leu Gln Lys Asp Phe Gly Leu Tyr Val Val
                370                 375                 380

Asn Met Phe Asp Thr His Gln Ala Ala Arg Leu Leu Asn Leu Gly Arg
385                 390                 395                 400

His Ser Leu Asp His Leu Leu Lys Leu Tyr Cys Asn Val Asp Ser Asn
                    405                 410                 415

Lys Gln Tyr Gln Leu Ala Asp Trp Arg Ile Arg Pro Leu Pro Glu Glu
                420                 425                 430

Met Leu Ser Tyr Ala Arg Asp Asp Thr His Tyr Leu Leu Tyr Ile Tyr
                435                 440                 445

Asp Lys Met Arg Leu Glu Met Trp Glu Arg Gly Asn Gly Gln Pro Val
450                 455                 460

Gln Leu Gln Val Val Trp Gln Arg Ser Arg Asp Ile Cys Leu Lys Lys
465                 470                 475                 480

Phe Ile Lys Pro Ile Phe Thr Asp Glu Ser Tyr Leu Glu Leu Tyr Arg
                    485                 490                 495

Lys Gln Lys Lys His Leu Asn Thr Gln Gln Leu Thr Ala Phe Gln Leu
                500                 505                 510

Leu Phe Ala Trp Arg Asp Lys Thr Ala Arg Arg Glu Asp Glu Ser Tyr
                515                 520                 525

Gly Tyr Val Leu Pro Asn His Met Met Leu Lys Ile Ala Glu Glu Leu
                530                 535                 540

Pro Lys Glu Pro Gln Gly Ile Ile Ala Cys Cys Asn Pro Val Pro Pro
545                 550                 555                 560

Leu Val Arg Gln Gln Ile Asn Glu Met His Leu Leu Ile Gln Gln Ala
                565                 570                 575

Arg Glu Met Pro Leu Leu Lys Ser Glu Val Ala Ala Gly Val Lys Lys
                580                 585                 590

Ser Gly Pro Leu Pro Ser Ala Glu Arg Leu Glu Asn Val Leu Phe Gly
                595                 600                 605

Pro His Asp Cys Ser His Ala Pro Pro Asp Gly Tyr Pro Ile Ile Pro
                610                 615                 620

Thr Ser Gly Ser Val Pro Val Gln Lys Gln Ala Ser Leu Phe Pro Asp
625                 630                 635                 640

Glu Lys Glu Asp Asn Leu Leu Gly Thr Thr Cys Leu Ile Ala Thr Ala
                    645                 650                 655

Val Ile Thr Leu Phe Asn Glu Pro Ser Ala Glu Asp Ser Lys Lys Gly
                660                 665                 670
```

-continued

```
Pro Leu Thr Val Ala Gln Lys Lys Ala Gln Asn Ile Met Glu Ser Phe
        675                 680                 685

Glu Asn Pro Phe Arg Met Ile Ser Asn Arg Trp Lys Leu Ala Gln Val
        690                 695                 700

Gln Val Gln Lys Asp Ser Lys Glu Ala Val Lys Lys Ala Ala Glu
705                 710                 715                 720

Gln Thr Ala Ala Arg Glu Gln Ala Lys Glu Ala Cys Lys Ala Ala Ala
                725                 730                 735

Glu Gln Ala Ile Ser Val Arg Gln Gln Val Val Leu Glu Asn Ala Ala
                740                 745                 750

Lys Lys Arg Glu Arg Ala Thr Ser Asp Pro Arg Thr Thr Glu Gln Lys
        755                 760                 765

Gln Glu Lys Lys Arg Leu Lys Ile Ser Lys Lys Pro Lys Asp Pro Glu
        770                 775                 780

Pro Pro Glu Lys Glu Phe Thr Pro Tyr Asp Tyr Ser Gln Ser Asp Phe
785                 790                 795                 800

Lys Ala Phe Ala Gly Asn Ser Lys Ser Lys Val Ser Ser Gln Phe Asp
                805                 810                 815

Pro Asn Lys Gln Thr Pro Ser Gly Lys Lys Cys Ile Ala Ala Lys Lys
                820                 825                 830

Ile Lys Gln Ser Val Gly Asn Lys Ser Met Ser Phe Pro Thr Gly Lys
        835                 840                 845

Ser Asp Arg Gly Phe Arg Tyr Asn Trp Pro Gln Arg
850                 855                 860
```

ANTIGENS ASSOCIATED WITH POLYMYOSITIS AND WITH DERMATOMYOSITIS

CROSS-REFERENCE TO RELATED APPLICATIONS

This is a continuation-in-part of U.S. patent application Ser. No. 07/579,023 filed on Sep. 7, 1990 by Ira N. Targoff and Qun Ge, now abandoned in favor of U.S. patent application Ser. No. 07/975,902.

BACKGROUND OF THE INVENTION

This relates to human antigens that can be used for the diagnosis of myositis and myositis-overlap syndromes that have an autoimmune pathogenesis and more particularly relates to the Mi-2 and PM-Scl antigens.

Autoimmune disorders arise when the immune system reacts against its own tissues. Autoimmune diseases are often classified on the basis of whether a single organ or tissue is involved or whether multiple organs or tissues are involved. Generalized or systemic autoimmune diseases, such as systemic lupus erythematosus (SLE), characterized by the involvement of multiple organs and tissues, are often associated with the presence of autoantibodies to fundamental cellular components. Other autoimmune diseases are characterized by autoantibodies to antigens associated with a single organ or tissue.

Systemic autoimmune diseases are typically characterized by the presence of autoantibodies. Some of the autoantibodies associated with the particular disease may be disease specific and others may be common to many autoimmune diseases. For example, SLE, which is a prototypical immune disorder, is characterized by the presence of autoantibodies that are detectable in other autoimmune disease, such as anti-single-strand DNA antibodies, anti-histones antibodies, and anti-ribonuclear particle (RNP) antibodies, and also by the presence of autoantibodies that are SLE-specific, such as the anti-double-stranded DNA antibodies. Other systemic autoimmune disorders, such as rheumatoid arthritis and idiopathic inflammatory myopathies, are also characterized by the presence of autoantibodies in the sera of patients that react with fundamental nuclear and cytoplasmic intracellular components. As with SLE, some of these autoantibodies are associated with other autoimmune disorders and some are specifically associated with autoimmune myositis.

The idiopathic inflammatory myopathies polymyositis, dermatomyositis and the related overlap syndromes disorder, such as polymyositis-scleroderma overlap, are inflammatory myopathies that are characterized by chronic muscle inflammation and proximal muscle weakness. The muscle inflammation causes muscle tenderness, muscle weakness, and ultimately muscle atrophy and fibrosis as described by Plotz et al., *Annals of Internal Med.* 111:143–157 (1989). Also associated with the muscle inflammation are elevated serum levels of aldolase, creatine kinase, transaminases (such as alanine aminotransferase and aspartate aminotransferase) and lactic dehydrogenase. Other systems besides muscle can be affected by these conditions, resulting in arthritis, Raynaud's phenomenon, and interstitial lung disease. Clinically, polymyositis and dermatomyositis are distinguished by the presence of a characteristic rash in patients with dermatomyositis. Differences in the myositis of these conditions can be distinguished in some studies of muscle pathology.

Autoantibodies can be detected in about 90% of patients with polymyositis and dermatomyositis according to Reichlin and Arnett, *Arthritis and Rheum.* 27:1150–1156 (1984). Sera from about 60% of these patients form precipitates with bovine thymus or human spleen extracts on Ouchterlony immunodiffusion (ID), while sera from about 80% of these patients stain tissue culture substrates, such as HEp-2 cells, by indirect immunofluorescence (IIF) (Targoff and Reichlin, *Arthritis and Rheum.* 28:796–803 (1985); Nishikai and Reichlin *Arthritis and Rheum.* 23:881–888 (1980); Reichlin et al., *J. Clin. Immunol.* 4:40–44 [1984]). There are numerous precipitating autoantibody specificities in myositis patients, but each individual antibody specificity occurs in only a fraction of the patients.

Many autoantibodies associated with myositis or myositis-overlap syndrome have been defined and in some cases the antibodies have been identified. These include antibodies that are present in other disorders and also disease-specific antibodies as described by Targoff and Reichlin, *Mt. Sinai J. of Med.* 55:487–493 (1988). Characteristic antibodies and their respective specificities are listed in Table 1. For example, a group of myositis-associated autoantibodies have been identified which are directed at cytoplasmic proteins that are related to tRNA and protein synthesis, particularly aminoacyl-tRNA synthetases. These include anti-Jo-1, which is directed against histidyl-tRNA synthetase and is the most common autoantibody associated with myositis autoimmune disorders (about 20% of such patients according to Nishikai and Reichlin, *Arthritis Rheum.* 23:881–888 [1980]); anti-PL-7, which is directed against threonyl-tRNA synthetase; and anti-PL-12, which is directed against alanyl-tRNA synthetase. A characteristic group of features is associated with anti-synthetases (Love et al., *Medicine* 70:360–374 [1991]). Anti-U1 RNP, which is frequently found in patients with SLE, may also be found in mixed connective tissue disease, overlap syndromes involving myositis, or in some cases of myositis alone. This antibody reacts with proteins that are uniquely present on the U1 small nuclear ribonucleoprotein, one of the nuclear RNPs that are involved in splicing mRNA. Autoantibodies that are associated with other conditions are sometimes found in patients with overlap syndrome such as anti-Sm, anti-Ro/SSA and anti-La/SSB. Anti-Ku has been found in myositis-scleroderma overlap syndrome and in SLE. The Ku antigen is a DNA binding protein complex with two polypeptide components, both of which have been cloned. Anti-Jo-1 and other anti-synthetases are disease-specific. Other myositis-associated antibodies are anti-PM-Scl, which is present in about 5–10% of myositis patients, many of whom have polymyositis-scleroderma overlap, and anti-Mi-2, which is present in about 8% of myositis patients, almost exclusively in dermatomyositis. Anti-Mi-2 is found in high titer in about 20% of all dermatomyositis patients and in low titer, by ELISA only, in less than 5% of polymyositis patients (Targoff and Reichlin, *Mt. Sinai J. of Med.* 55:487–493 [1988]).

Anti-Mi was first described by Reichlin and Mattioli, *Clin. Immunol. and Immunopathol.* 5:12–20 (1976). A complement-fixation reaction was used to detect it and, in that study, patients with dermatomyositis, polymyositis and polymyositis overlap syndrome had positive reactions. The prototype or reference serum, from patient Mi, forms two precipitin lines on immunodiffusion (ID) with calf thymus antigens, Mi-1 and Mi-2. Mi-1, which has been purified from bovine thymus nuclear extracts (Nishikai et al., *Mol. Immunol.* 17:1129–141 [1980]) is rarely found in other sera and is not myositis specific (Targoff et al., *Clin. Exp. Immunol.* 53:76–82 [1983]).

Anti-Mi-2 was found to be a myositis-specific autoantibody by Targoff et al., *Arthritis and Rheum.* 28:796–803

(1985). Furthermore, all patients with the precipitating antibody have the dermatomyositis rash. It is therefore potentially important as a diagnostic tool and, perhaps, ultimately as a tool for understanding the disease etiology. Anti-Mi-2 is also the only antibody response that appears to be selective for dermatomyositis and not for other subgroups of inflammatory myopathy without skin involvement.

Bovine thymus Mi-2 antigen was originally found to be a nuclear protein that separates in SDS polyacrylamide (SDS-PAGE) gels into two bands with apparent molecular weights of 53 kilodaltons (hereinafter kDa) and 61 KDa, respectively. Recently, additional higher molecular weight bands have been found. The bovine thymus antigenic activity is destroyed by SDS-PAGE and is trypsin sensitive, but not RNAse sensitive (Targoff et al., *Arthritis and Rheum.* 28:796–803 [1985]). Its nature and function have not as yet been identified.

Anti-PM-1 was first identified as an antibody found in 61% of dermatomyositis/polymyositis patients, including patients with polymyositis-scleroderma overlap (Wolfe et al., *J. Clin. Invest.* 59:176–178 [1977]). Anti-PM-1 was subsequently shown to be more than one antibody. The unique specificity component of anti-PM-1 was later named anti-PM-Scl (Reichlin et al., *J. Clin. Immunol.* 4:40–44 [1984]). Anti-PM-Scl is found in the sera of about 5–10% of myositis patients, but is most commonly associated with polymyositis-scleroderma overlap syndrome. It also occurs in patients with polymyositis or dermatomyositis alone or in patients with scleroderma without myositis.

Anti-PM-Scl antibody immunoprecipitates a complex from HeLa cell extracts of at least eleven polypeptides that have molecular weights ranging from about 20 to 110 kDa as described by Reimer et al., *J. Immunol.* 137:3802–3808 (1986), and possibly up to 16 polypeptides as described by Gelpi et al., *Clin. Exp. Immunol.* 81:59–64 (1990). The antigen is trypsin-sensitive, occurs in nucleoli (Targoff and Reichlin, *Arthritis Rheum.* 28:226–230 [1985]) and is believed to be a pre-ribosomal particle.

In an abstract, Bluthner, et al., *First Int. Workshop on the Mol. and Cell Biology of Autoantibodies and Autoimmunity* in Heidelberg (Springer-Verlag, Jul. 27–29, 1989) reported that sera from patients suffering from polymyositis/scleroderma-overlap syndrome (PM/Scl) recognize two major nucleolar proteins of 95 and 75 kDa molecular weight in Western blots of a HeLa cell extract. They also reported that cDNA that encodes a 20 kDa protein reactive with autoantibodies eluting from the 95 kDa PM-Scl HeLa antigen subunit had been cloned from a HeLa cDNA library.

Alderuccio et al., *J. Exp. Med.* 173:941–952 (1991), have cloned and sequenced the 75 kDa component of the PM-Scl antigen. The "75 kDa" was found to be a protein of 39.2 kDa that migrates aberrantly on polyacrylamide gel electrophoresis (PAGE) because of a region that is rich in acidic residues at the carboxyl half of the molecule.

TABLE 1

Autoantibodies to Nuclear and Cytoplasmic Antigens in Dermatomyositis and Polymyositis Patients[1]

| Antibody | % of Patients | Characteristic Subgroup |
|---|---|---|
| Group A | | |
| Anti-Jo-1 (his-tRNA synthetase) | 18 | PM-ILD |
| Anti-PM-Scl | 8 | PM-Scleroderma |
| Anti-Mi-2 | 8 | DM |
| Anti-PL-7 (thr-tRNA synthetase) | 3 | PM-ILD |
| Anti-PL-12 (ala-tRNA-synthetase) | 3 | PM-ILD |
| Anti-SRP (signal recognition particle) | uncommon | PM |
| Anti-Fer, Mas, etc. (other tRNA associated antigens) | rare | PM |
| Anti-56 kD | 80–90% | all |
| Group B | | |
| Anti-nRNP (U1 small nuclear RNP) | 13 | Overlap |
| Anti-Ro/SS-A | 7 | overlap |
| Ro/SSA + La/SSB | 2 | Sjögren's, SLE |
| Anti-cytoskeletal | 86 | all |
| Anti-Ku | <1 | Overlap |

[1]Targoff and Reichlin (1988), Mt. Sinai J. of Med. 55: 487–493, 488.
PM, polymyositis.
DM, dermatomyositis.
ILD, interstitial lung disease.
Group A - autoantibodies that are usually found in serum from patients with myositis or myositis overlap syndromes.
Group B - more common in other conditions, but also occurring PM/DM.

The antibodies set forth in Group A of Table 1 serve as useful diagnostic markers because of their high specificity for myositis and its subgroups. At the present time, however, it is difficult and time consuming to routinely screen sera for the presence of these antibodies because standard serum needed for comparison is not widely available and highly concentrated tissue extracts must be used and the technique of immunodiffusion is slow and insensitive. Both anti-PM-Scl and anti-Mi-2 give only weak reactions in immunodiffusion, making them even more difficult to detect. In addition, these screening assays generally use the corresponding bovine antigen (which is more readily available for clinical purposes), which may not detect the presence of autoantibodies that do not cross-react sufficiently to be detectable.

There is, thus, a need to obtain the human myositis-specific antigens, such as the Mi-2 antigen and the PM-Scl antigen, in purified form, and plentiful, readily available amounts so that rapid, accurate, and convenient diagnostic assays can be developed. Recent studies with other antigens such as anti-Jo-1 have indicated a correlation of antibody level with disease activity, as reported by Miller, et al., *J. Clin. Invest.* 85:468–475 (1990). Quantitative assays for these antibodies may help assess disease activity if similar findings are observed for these antibodies. In addition, elucidation of the biochemical structure and function of the particular disease-specific antigen at which the immune response is directed may aid in understanding the etiology of the disease and in the development of effective treatments. Also, since these antigens are conserved cellular proteins, they are likely to be functionally important proteins. Study and identification of these antigens may provide significant insights into nuclear and nucleolar processes.

It is therefore an object of this invention to provide DNA encoding antigens that are specifically recognized by myositis-specific autoantibodies which can be expressed in large quantities and the proteins easily purified.

It is a further object of the invention to provide human antigens or portions thereof for use in diagnostic assays and as tools for studying autoimmune myositis.

It is another object of the invention to provide methods for detecting autoantibodies that are uniquely found in the sera of individuals with dermatomyositis or myositis-scleroderma overlap.

SUMMARY OF THE INVENTION

Immunoassays for detecting myositis specific antibodies which will help in diagnosis of dermatomyositis (DM), polymyositis (PM), and myositis-sclerosis overlap are provided. Isolated DNA molecules that encode Mi-2 and PM-Scl antigens or antigenic portions thereof, DNA probes for isolating cDNA or genomic DNA clones that encode such antigens or portions thereof, the antigens encoded by the isolated DNA, and diagnostic assays for detecting anti-Mi-2 and anti-PM-Scl autoantibodies in sera are also provided.

DNA that encodes a protein that includes at least one epitope of the human Mi-2 antigen and DNA that encodes the 100–110 kDa subunit of the human PM-Scl antigen have been cloned from a human cDNA library. This DNA can be used to provide proteins that include epitopes of the human Mi-2 and PM-Scl antigens which can be used in assays for autoantibodies to these epitopes, or for other purposes. In addition, this DNA is used to provide probes to screen cDNA and genomic libraries in order to isolate DNA that encodes additional portions of the human antigens or DNA that spans each gene, or to obtain DNA that encodes related antigens in humans and other mammals. The DNA that encodes additional portions of the antigens, and the proteins encoded thereby, may be used in immunodiagnostic assays in order to identify patients that express anti-Mi-2 autoantibodies that do not react with the originally cloned epitopes.

The Mi-2 antigenic epitopes encoded by the DNA, or a portion of them, is useful in immunodiagnostic assays, including ELISAs, dot blots, immunodiffusion, radioimmunoassays and immunoprecipitation assays, to detect anti-Mi-2 to help in diagnosing dermatomyositis. The PM-Scl antigen encoded by the DNA, or a portion of the antigen, is useful in similar assays to help in diagnosing polymyositis and polymyositis-scleroderma overlap disorders.

BRIEF DESCRIPTION OF THE DRAWINGS

FIG. 1 is a restriction enzyme map of clone JH2 showing the location of cleavage sites for TaqI, KpnI, XhoI, and SmaI, and PstI. Fragments from double digestions with KpnI and TaqI; and XhoI and PstI, are defined.

DETAILED DESCRIPTION OF THE INVENTION

Figure 2:
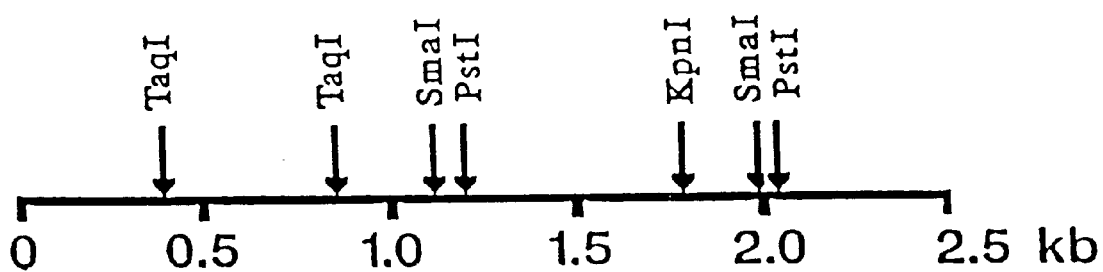
FIG. 2 is a restiction enzyme map of the cleavage sites on the original JH4 cloned cDNA insert for the enzymes used to produce the fragments that were sequenced.

Characteristics of the Myositis-specific Antigens
A. Identification and Characterization of PM-Scl Antigens.

The PM-Scl antigen was originally defined by a standard serum containing antibody that reacted with a previously undefined antigen in immunodiffusion against bovine tissue extract. Immunodiffusion can determine unequivocally, by reactions of identity, that two sera contain antibodies to the same antigen even when that single antigen is mixed with thousands of others in a concentrated tissue extract. A reaction of non-identity can determine that two sera react with different antigens. PM-Scl antigen was defined as the antigen in tissue extracts that reacts with the standard anti-PM-Scl serum. A second serum has anti-PM-Scl if it shows a reaction of identity with the standard serum (or a known positive validated by reaction of identity with the standard serum) in immunodiffusion.

Bovine PM-Scl antigen is PM-Scl antigen derived from bovine tissue. Human PM-Scl antigen is PM-Scl antigen derived from human tissue. It is expected that it will be better to use human antigen for testing since it is known that more patients react with the human form of some autoantigens, such as human Ro/SSA antigen than react with the bovine form. Reaction of anti-Jo-1 with human Jo-1 is also stronger than with bovine Jo-1.

The human PM-Scl antigen appears to be a particle consisting of at least eleven polypeptides, as determined by immunoprecipitation by Reimer et al., *J. Immunol.* 137:3802–3808 (1986). Gelpi et al., *Clin. Exp. Immunol.* 81:59–64 (1990) found 16 polypeptides. The PM-Scl antigen has not been purified. Anti-PM-Scl antibody immunoprecipitates from HeLa cell extract a complex of between eleven and sixteen polypeptides that have molecular weights ranging from about 20 to 110 kDa, as discussed in the background of the invention. The antigen is trypsin-sensitive, occurs in nucleoli, and there is some evidence suggesting that it may be a pre-ribosomal particle.

B. Characteristics of the Mi-2 antigen.

Because anti-Mi-2 is specific for dermatomyositis, assays that detect the presence of these antibodies in human serum are useful for diagnosing dermatomyositis. Standard immunoassays, such as ELISAs, Ouchterlony immunodiffusion and other assays that are known to those of skill in the art, provide a useful repertoire for such diagnosis. The purified human Mi-2 antigen, peptides that include at least one epitope that is recognized by the respective autoantibodies, and/or proteins expressed from DNA that encodes at least one such epitope are, therefore, preferred components for any accurate and reliable diagnostic assay.

Bovine Mi-2 antigen had an apparent molecular weight of two to three million, when measured using fast protein liquid chromatography gel filtration (FPLC). This is more than ten times the molecular weight of the largest band seen on SDS-PAGE gels of the antigen, which suggests that the purified bovine antigen is a complex of multiple copies of the components or a multimeric aggregate of many identical protein complexes that dissociate in SDS. SDS-PAGE of the immunoprecipitated human and purified bovine Mi-2 antigens indicates that both antigens are complexes consisting of multiple subunit proteins.

When purified by affinity chromatography, SDS-PAGE of the bovine antigen shows a high molecular weight band in the region of 200–240 kDa, and a band at 150 kDa. A very strong band is seen at 107 kDa and another at 40 kDa. When the preparation is separated by gel filtration on FPLC, the 200 and 40 kDa bands are seen in the same fraction, suggesting that they are complexed. This fraction is active in ELISA. The 150 kDa band and 107 kDa band are not as consistently active in ELISA. No bands are active by Western blot against anti-Mi-2 sera.

The human antigen has not been purified. The human antigen has been analyzed by immunoprecipitation using HeLa cell extracts. A high molecular weight band in the 200–240 kDa range is often seen, and a 150 kDa band is sometimes seen. Bands at 62 kDa and 65 kDa are usually seen in some gels, but a 40 kDa band is not seen. The most consistent band seen by immunoprecipitation from HeLa extract is 200–240 kDa. A similar band is seen with the bovine antigen but is less prominent than the 40 kDa band. There is no reaction with HeLa extract in Western blot by anti-Mi-2 sera. Thus, the high molecular weight bands of approximately 200–240 kDa are shared by bovine and HeLa forms of Mi-2 and may be the crucial components.

When the affinity purified bovine antigen is subjected to FPLC purification, the high molecular weight bands and the 40 kDa molecular weight band remain together, while the two other bands are separated. It is possible that one or more of the other components are degradation products. However, because protease inhibitors do not affect the amounts of the lower molecular weight bands, it is likely that the lower molecular weight bands are independent components of the Mi-2 complex, which is dissociated in reducing conditions, rather than proteolytic breakdown products of the higher molecular weight proteins. The pattern of bands observed on the SDS polyacrylamide gels is reproducible and consistent for antigen prepared using the same immunosorbent column and also for antigen that is purified using IgG derived from sera from different patients. It is, therefore, probable that all of the observed bands in the purified antigen relate to Mi-2.

The antigenicity of the protein subunits of the bovine Mi-2 antigen is most consistently associated with the fractions of immunoaffinity purified antigen and FPLC purified antigen that include the proteins of molecular weights of 249, 198, 152 and 40 kDa. The three highest molecular weight bands are also seen on $^{35}$S-methionine-labeled immunoprecipitates from bovine thymus extracts. Western blots of the separated proteins, however, do not react with any antibodies in any sera that has been tested. This suggests that the reactive epitope in the antigen is conformational and is not present in the denatured and reduced form of the antigen complex. Alternatively, it is possible that the epitope is composed of more than one peptide and that dissociation of a complex of proteins destroys the immunoreactivity. Because all sera share this property, the anti-Mi-2 autoantibodies that have been identified by screening with bovine thymus extracts may share common epitopes. The reaction of Mi-2 autoantibodies in immunodiffusion assays indicate that these antibodies must recognize multiple epitopes, because immune precipitation requires lattice formation.

The human and bovine Mi-2 antigens must be sufficiently similar for at least some autoantibodies against Mi-2 that are present in human sera to cross-react with the bovine Mi-2 antigen. Because the bovine and human Mi-2 antigens appear to include different subunits, as analyzed by different methods as described above, it is possible that a percentage of patients that might have autoantibodies that react with Mi-2 are not identified with assays that use bovine thymus extract. This is particularly significant with respect to Mi-2, because the epitope that is recognized by autoantibodies appears to be conformationally dependent and the subunit structure of the human antigen differs from that of the bovine antigen.

The human and bovine PM-Scl antigens and the human and bovine Mi-2 antigens are antigenically related since at least some autoantibodies against each of these antigens that are present in human sera react with the corresponding bovine antigen. However, it is unknown whether the autoantibodies of all individuals with anti-PM-Scl or anti-Mi-2 cross react with the corresponding bovine antigens and whether unique epitopes exist on the human antigens.

It is expected that diagnostic assays that employ the human antigens or proteins that include at least one epitope of the antigens as the diagnostic reagent will be more specific and reliable than similar assays that use bovine thymus nuclear extracts as the diagnostic reagent and may be useful for diagnosing myositis in patients whose myositis-specific autoantibodies do not react with the bovine antigen.

Cloning of DNA that Encodes at Least One Epitope of Human Myositis-specific Antigens, PM-Scl and Mi-2

In order to obtain the human Mi-2 and PM-Scl antigens, or proteins that include at least one epitope thereof, in sufficient quantity for use in diagnostic assays, DNA that encodes all or a portion of each antigen has been cloned. Because the human antigens have not been purified and are not well-characterized, probes based on the protein sequence cannot be prepared nor can assays for the protein be devised, because biological activities of the antigens are unknown.

Multiple sera that contain only autoantibody to Mi-2 antigen and sera that contain only autoantibody to PM-Scl antigen have been painstakingly collected at the University of Oklahoma Health Science Center, Oklahoma City, Okla., over the course of many years. In addition, sera from over 500 other patients with either DM or PM have been collected. Most of these sera have been tested for the various myositis autoantibodies. This very large and unique collection of sera, in particular of anti-Mi-2 sera, was essential in identifying cDNA for anti-Mi-2 and anti-PM-Scl.

An advantage of the cloned antigens is the ease of preparation of the antigen for use in ELISA. ELISA has advantages over other techniques for quantitation of antibody, which can be used to determine antibody titer and correlation with disease activity, if any. The cloned antigen can also be used to simplify detection of the antigen in a dot blot assay, which cannot be done with whole extract. A dot blot assay can be modified to a "dip-stick" type of test to make it even more simple and incorporate it into a test for multiple specificities at once.

In order to clone DNA that encodes the human Mi-2 and PM-Scl antigens, a human expression library was screened with serum that contains anti-Mi-2 autoantibodies and also with serum that contains anti-PM-Scl autoantibodies. Clones having DNA that encodes a protein reactive with the screening serum were selected.

The cloned DNA may be used for expressing portions of the myositis-specific antigens that react with antibodies that do not cross-react with the bovine antigens, and may be used in methods for diagnosing myositis or related conditions.

Assays Using the Cloned Proteins and the Nucleic Acids Encoding the Proteins A. The Cloned and Expressed Proteins.

Once the clones that encode proteins reactive with anti-Mi-2 sera and/or anti-PM-Scl sera have been isolated, they can be expressed using methods known to those skilled in the art. The expressed proteins can be used in immunoblot assays, such as dot blot assays, including any solid phase assay in which the antigenic reagent is transferred to nitrocellulose prior to reaction with the test sample. The antigen reagent may be dotted directly onto the nitrocellulose or electrophoresed into a gel and transferred to the nitrocellulose.

Dot blot assays are more useful than conventional Western blot assays for testing reactions with epitopes that are conformationally dependent because they do not involve denaturing gels. In a dot blot assay, the reactive protein or peptide is dissolved or suspended in a non-denaturing buffered solution and spotted onto nitrocellulose filters until a sufficient amount is bound to the nitrocellulose to bind to any antibodies that may be present in low concentration. Alternatively, host cells, such as E. coli or eukaryotic cells (either mammalian cells or yeast cells), that contain DNA that encodes the protein or peptide that includes at least one epitope, are incubated under conditions whereby the protein is expressed. Typically, the cells are then gently lysed, spun to remove cell debris, and the supernatant dotted on nitrocellulose prior to reaction with the test sample. Usually some purification of the expressed protein is required in order to remove possible confounding reaction with the protein of the host cell.

In either embodiment, the amount of antigen or lysate dotted onto the nitrocellulose is a function of the particular type of assay. If the purpose of the assay is merely detection of the antibody, then, in order to drive the reaction, an excess of antigen is bound to the nitrocellulose filter. The types of assays and the conditions under which each type must be run are known to those of skill in the art and are readily ascertainable by one of skill in the art.

Blots in which the antigen is first electrophoresed under denaturing conditions onto polyacrylamide gel, known to those of skill in the art as Western blots, are not useful for detecting antibodies that bind to conformationally dependent epitopes but are useful for identifying or characterizing by molecular weight a particular portion, component or subunit of an antigen to which an antibody binds. After electrophoresis, the proteins on the gel are transferred to nitrocellulose, by any method known to those of skill in the art, for example, as described by Towbin et al. *Proc. Natl. Acad. Sci. USA* 76:4350–4354 (1979).

After transfer from a gel or after dotting the antigen reagent onto the nitrocellulose, excess protein binding sites on the nitrocellulose are blocked by binding known proteins, such as 5% bovine dry non-fat milk, albumin or serum, that do not bind to the antigen reagent. Methods and reagents for blocking are well-known to those of skill in the art. The blocked nitrocellulose is then incubated with the test sample under conditions whereby autoantibodies that recognize the epitope or epitopes present on the antigen form complexes with the antigen. The nitrocellulose is then washed and treated so that the complexes may be detected. Detection may be effected by any method known to those of skill in the art. For example, to detect human autoantibodies, a goat anti-human immunoglobulin antibody may be used in a form in which it is conjugated to an enzyme, usually alkaline phosphatase or horse-radish peroxidase, and then a substrate is added that will deposit permanent color at sites where enzyme is present, specific to the particular enzyme. For example, for alkaline-phosphatase, a BCIP-NBT substrate may be used. Any convenient label, such as a radiolabel or an enzyme, may be used.

The cloned antigens can also be used in ELISAs, using methods known to those skilled in the art.

B. Probes Derived From the Cloned DNA.

Using standard procedures that are well-known to those of skill in the art, DNA probes may be prepared from the selected clones and used to screen an appropriate human cDNA library. A clone, or a series of clones, that include DNA that spans the entire gene for each antigen may be selected. The DNA probes may also be used to screen a genomic library in order to obtain genomic DNA that encodes all or a portion of the antigen or to screen genomic or cDNA libraries from human or other mammals in order to obtain DNA that encodes proteins that include sequences of amino acid that are related to the human Mi-2 and Pm-Scl antigens or epitopes thereof. Any of this DNA may then be used to produce proteins that may be used in diagnostic assays, such as those described above.

Definitions

Unless defined otherwise, all technical and scientific terms used herein have the same meaning as is commonly understood by one of ordinary skill in the art to which this technology belongs. All publications and U.S. Patents referenced herein are specifically incorporated by reference thereto.

As used herein, immunodiagnostic assays include assays that in some manner utilize the antigen-antibody interaction to detect and/or quantify the amount of a particular antibody that is present in a test sample to assist in diagnosis of disease. There are many such immunoassays known to those of skill in the art. As used herein, however, the antigens and DNA of this disclosure may be substituted for the corresponding reagents in the otherwise known assays, whereby the modified assays may be used to detect and/or quantify autoantibodies that were heretofore difficult or not possible to detect. It is the use of these reagents, the antigens and DNA, that permit modification of known assays for detection of autoantibodies associated with autoimmune myositis or related conditions to help in diagnosis. Such assays include, but are not limited to ELISAs, immunodiffusion assays, and immunoblots. Suitable methods for practicing any of these assays are known to those of skill in the art. Typical protocols for conducting ELISAs, immunoblots, and immunoprecipitation assays are described in the Examples.

As used herein, the antigen, or a protein that includes at least one epitope of the antigen, can be used as the diagnostic reagent. The diagnostic reagents prepared in accordance with this disclosure may be substituted for bovine thymus extracts, HeLa cell extracts or any other antigenic reagent known to those of skill in the art of immunodiagnostic assays for the detection of anti-Mi-2 and anti-PM-Scl antibodies. An epitope is defined as a portion of a protein, polypeptide or peptide that is specifically recognized by an antibody. It may consist of any number of amino acids and it may be dependent upon the primary, secondary or tertiary structure of a protein. In accordance with this disclosure, a protein or peptide that includes at least one epitope of the Mi-2 or PM-Scl antigen, may be used as reagents in the immunodiagnostic assays. For example, the DNA sequence set forth in Sequence Listing ID No. 1 encodes a protein that includes at least one Mi-2 epitope, and the DNA sequence set forth in Sequence Listing ID No. 3 encodes a protein that includes at least one PM-Scl epitope. Accordingly, such protein or product produced by expressing the cloned DNA may be used in an assay that utilizes the specific interaction between an anti-Mi-2 autoantibody and such protein.

As used herein, a protein or peptide that includes at least one epitope may contain any sequence of amino acids as long as it includes a portion that has the primary, secondary or tertiary structure that is recognized by a particular antibody. Experimental and computational methods whereby such epitopes may be identified are known to those of skill in the art. Methods and algorithms whereby such epitopes may be identified are known to those of skill in the art. Also encompassed within this class of proteins or peptides is any modifications of such proteins or peptides that do not substantially alter the specificity and extent of the interaction between such protein and the antibody.

As used herein, myositis antigens refer to antigens that are the target of myositis-associated autoantibodies. These antigens may be used to detect these antibodies, thereby assisting in diagnosing autoimmune myositis. Any protein that includes at least one such epitope is encompassed by the term myositis-specific antigen.

As used herein, the DNA falling within the scope of this disclosure is any DNA that encodes a protein including one or more epitopes present on Mi-2 or PM-Scl antigens. The DNA may be genomic DNA, in which case it may include introns, or it may be cDNA which is prepared in vitro from mRNA using a reverse transcriptase and which contains open reading frames. Methods for isolation, cloning or synthesizing DNA and cDNA are well known to those of skill in the art. Expression refers to the process by which nucleic acid is transcribed and translated into peptides, polypeptides, or proteins. If the nucleic acid is derived from genomic DNA, expression may, if an appropriate eukaryotic host cell or organism is selected, include splicing of the mRNA and subsequent glycosylation. An expression vector refers to a recombinant DNA or RNA construct, such as a plasmid, a phage, recombinant virus or other vector that, upon introduction into appropriate host cells, is capable of transcribing nucleic acid molecules that have been cloned into the vector, and then translating the transcribed nucleic acid into a polypeptide. The nucleic acid molecule is cloned into the vector in such a manner that it is operably linked to regulatory sequences that are capable of effecting expression of the heterologous nucleic acid molecules. Upon expression in a selected host cell or organism, if the appropriate regulatory sequences are operably linked to the DNA or included in the heterologous DNA, the expression product may be exported to the cytoplasm and/or may be secreted out of the host cell.

Appropriate expression vectors are well-known to those of skill in the art and include those that are replicable in eukaryotic cells and/or prokaryotic cells. Such expression vectors may remain episomal or may integrate into the host cell genome.

As used herein, a DNA probe is a DNA molecule that includes a sufficient number of nucleotides to specifically hybridize under non-stringent conditions to DNA or RNA that includes identical or closely related sequences of nucleotides. A probe may include any number of nucleotides and may include as few as about 10 and as many as hundreds of thousands of nucleotides. The conditions and protocols for such hybridization reactions are well-known to the those of skill in the art, as are the effects of probe size, temperature, degree of mismatch, salt concentration and other parameters on the hybridization reaction. For example, the lower the temperature and higher the salt concentration at which the hybridization reaction is carried out, the greater the degree of mismatch that may be present in the hybrid molecules.

As used herein, all assays and procedures, such as hybridization reactions and antibody-antigen reactions, unless otherwise specified, are conducted under conditions recognized by those of skill in the art as standard conditions.

The myositis-specific antigens and immunoassays for detecting myositis specific antibodies will be further understood with reference to the following non-limiting examples.

EXAMPLE 1

Immunoprecipitation and Characterization of the Human Mi-2 Antigen

Plasma containing anti-Mi-2 antibodies from a patient with dermatomyositis was provided by Dr. Frank Arnett from the University of Texas Health Sciences Center at Houston. Other sera were obtained from patients with dermatomyositis from the collection of myositis sera at the University of Oklahoma Health Science Center. The sera were identified as having the Mi-2 antibody by identity in Ouchterlony immunodiffusion (ID) against bovine thymus extract with a reference serum that had been confirmed using the original Mi prototype serum. Sera from normal laboratory workers were used as controls. Disease control samples were taken from other patients at Oklahoma University Health Sciences Center. Reference sera for other autoantibodies were also confirmed by ID.

HeLa cell extract was prepared by labeling $2\times10^6$ cells (one small 25 cm$^2$ flask) with 500 $\mu$Ci of $^{35}$S-Met in 2.5 ml of met-deficient minimal essential media with 10% fetal calf serum for 16 hours. The cells were removed with trypsin, pelleted, washed with phosphate buffered saline (PBS), and then resuspended in lysis buffer (NET-2 with 1% NANIDET™ P-40 (ethylphenylpolyethylene glycol). After centrifugation at 10,000×g for 15 minutes, the supernatant was added to the IgG coated beads. One flask provided extract for ten samples.

Twenty-five $\mu$l of patient serum was incubated with 30 $\mu$l of a 1:1 (v/v) suspension of pre-swollen protein A-agarose (Boehringer-Mannheim) in 500 $\mu$l of buffer containing 10 mM Tris-HCl pH 8.0, 0.5 M NaCl, and 0.1% NP-40 immunoprecipitation buffer (IPPB) for 2 hours at 4° C. The beads were then washed three times with 50 mM Tris-HCl pH 7.4, 150 mM NaCl, 0.05% NP-40 (NET-2) prior to incubation with extract. The washed immunoprecipitates were suspended in sample buffer, containing 0.2% SDS and 5% mercaptoethanol, heated at 100° C. for 5 minutes and were analyzed by electrophoresis on a SDS-10% polyacrylamide gel prepared according to the method of Laemmli, *Nature* 227:680 (1970), using a discontinuous buffer system. The gels were developed by autoradiography.

Immunoprecipitates from the HeLa extract using anti-Mi-2 sera were run on the gel and compared to immunoprecipitates using normal human serum and sera known to contain the autoantibodies OJ (antibody to isoleucyl-tRNA synthetase), PL-12, Ro, La, and PL-7, but not Mi-2.

The autoradiograms were exposed for 48 hours in order to detect the distinct pattern of proteins immunoprecipitated by anti-Mi-2. Although the bands were weak and often difficult to distinguish from background or artifact, comparison of immunoprecipitates obtained using multiple positive sera revealed a characteristic pattern. A series of 5 bands of 249, 198, 152, 67, and 62 kDa, which were called a, a', b, c, and d, respectively, was precipitated by 10 different anti-Mi-2 containing-sera. None of the three high molecular weight bands (a, a', and b) was seen in parallel lanes from normal or other myositis sera. Control sera that contained autoantibodies to Jo-1 and Ro/SSA immunoprecipitated proteins of 52 or 50 kDa, but did not precipitate proteins that corresponded to those immunoprecipitated by anti-Mi-2 sera.

EXAMPLE 2

Purification of the Bovine Mi-2 Antigen from Bovine Thymus Extract

Fresh or frozen bovine thymus was homogenized in 2 volumes of cold PBS (10 mM phosphate buffer pH 7.2, 150 mM NaCl, 10 mM Na Azide) with 1.3 mM phenylmethylsulfonyl fluoride (PMSF) and 1.3 mM dithiothreitol (DTT) and extracted for 30 minutes. The homogenate was then centrifuged at 12,210×g for 2 hours, and the supernatant was filtered through cheesecloth.

The filtered supernatant was diluted with 2 volumes of 10 mM sodium phosphate buffer, pH 7.0 and then incubated with similarly equilibrated DEAE-cellulose (Whatman) for 1 hour. The resin was washed in a sintered glass funnel with 10 mM phosphate buffer, pH 7.0, and then with 0.1 M NaCl in 10 mM phosphate buffer pH 7.0. The antigen was then eluted with 0.2 M NaCl in phosphate buffer.

Antigenic activity was assayed by standard and inhibition enzyme linked immunosorbent assay (ELISA) and it eluted between 0.1 M and 0.2 M NaCl. Protein concentration was determined by the method of Bradford, *Anal. Biochem.* 72:248 (1976) using the Bio-Rad™ Protein (Richmond, Calif.) assay.

Two affinity adsorbents were prepared, each with the IgG fraction from a different serum that previously had been determined by ID and ELISA to have anti-Mi-2 autoantibodies. The IgG fraction of the anti-Mi-2 plasma was purified by DEAE-cellulose chromatography (DEAE 52, Whatman) and coupled to cyanogen bromide-preactivated Sepharose™ 4B (Pharmacia, Piscataway, N.J.). About 35 ml of plasma from each of the selected sera were loaded on the DEAE-cellulose, which had been equilibrated to pH 7.0. The flow-through fractions that contain protein (measured by absorbance at 280 nm) were pooled, concentrated and dialyzed against 0.1 M bicarbonate buffer, pH 8.3 with 0.5 M NaCl. About 65–70 mg of IgG were obtained from each 35 ml of plasma. The IgG was coupled at 5 mg IgG/ml gel to cyanogen bromide preactivated Sepharose™ 4B (Pharmacia, Uppsala Sweden) according to the manufacturer's instructions.

Greater than 90% coupling was achieved. The immunosorbent gel was then washed alternately with 0.1 M acetate pH 4.0 and 0.1 M $NaHCO_3$, pH 9.0, for three cycles followed by washing with 4 M $MgCl_2$. The gel was then equilibrated with TBS (50 mM Tris-HCl pH 7.2, 0.5 M NaCl, 10 mM Na Azide) and packed in a column prior to use.

The fractions from the DEAE column that contained Mi-2 antigenic activity, the 0.2 M NaCl eluate, were then loaded onto one of the two immunoaffinity resins, which was then washed with 2 liters of TBS until the absorbance of the flow through at 280 nm was below 0.05 units. Two column volumes of 4 M $MgCl_2$ were then applied to the column. Elution of the immunoaffinity chromatography column with 4 M $MgCl_2$ yielded a single broad protein peak. The fractions were pooled and dialyzed against 10 mM Tris-HCl pH 7.0, and concentrated to approximately 1 mg/ml. The affinity purified antigen retained maximal activity in ELISA at protein concentrations of 3 µg/ml and higher.

EXAMPLE 3

Analysis of the Bovine and Human Mi-2 Antigens

SDS-PAGE analysis, performed as described in Example 1, of the affinity purified bovine Mi-2 antigen revealed several bands. The relative intensity of the bands varied in different preparations, but the higher molecular weight bands at 250, 240, and 145 kDa were consistently fainter than the bands at 94, 65, and 40 kDa, while the 40 kDa band was usually the strongest. No bands corresponding to bands e or g of FIG. 1 were seen in the lanes in which the $^{35}$S-immunoprecipitated human antigen were loaded (see Example 1), but the 250, 240, 145 and 65 kDa bands were similar to those seen by immunoprecipitation.

Western blots of the purified bovine antigen were run against anti-Mi-2 sera. Samples of the purified antigens were run on Laemmli gels as described in Example 1, except that beta-mercaptoethanol at a final concentration of 5% was added to the sample buffer, followed by boiling for 5 minutes. The separated sample was then transferred to nitrocellulose in a Bio-Rad™ Trans-Blot apparatus (Bio-Rad, Laboratories, Richmond, Calif.) in 0.025 M Tris-0.192 M glycine buffer at pH 8.3 with 20% methanol.

Prior to binding the anti-Mi-2 serum, the nitrocellulose paper was blocked with 5% bovine dry non-fat milk in 0.010 M Tris, 0.15 M NaCl, pH 7.4, for 1 hour at 40° C. The anti-Mi-2 serum was diluted 1/100 in 5% bovine dry non-fat milk in 0.010 M Tris, 0.15 M NaCl, pH 7.4, and was reacted at room temperature for 2 hours or overnight at 4° C. with the nitrocellulose filters.

A conjugate of goat anti-human IgG/alkaline phosphatase (Sigma) diluted 1/500 in buffer was then applied. After washing, the nitrocellulose strip was placed in alkaline phosphatase substrate for 10 to 20 minutes and finally washed with methanol/water mixture. Silver staining was performed using the BioRad™ Silver Stain Kit (Richmond, Calif.).

Western blotting of the immunoaffinity purified antigen was consistently negative when developed with sera containing anti-Mi-2. Silver staining of the gel following transfer to nitrocellulose showed incomplete transfer of the 250, 240 and 145 kDa bands under all of the transfer conditions attempted. When partial transfer of these bands was achieved, the staining with patient sera remained negative. Western blotting against whole HeLa extract was also negative with all monospecific anti-Mi-2 sera tested. These results suggest that the epitope or epitopes in both the bovine and human Mi-2 antigen that are recognized by the anti-Mi-2 autoantibody in patient sera is dependent upon the secondary and/or tertiary structure of the subunits of the antigen.

EXAMPLE 4

Subunit Analysis of the Affinity-purified Bovine Mi-2 Antigen

The affinity-purified Mi-2 bovine antigen was analyzed using Sepharose™-12 gel filtration chromatography on a fast protein liquid chromatography (FPLC) apparatus (Pharmacia). Approximately 50 µg of immunoaffinity purified Mi-2 from bovine thymus was applied to a Sepharose™-12 10/30 gel filtration column, which had been equilibrated in 150 mM NaCl in 15 mM Tris-HCl buffer, pH 7.2, and eluted with the same buffer.

Typically four protein peaks, A, B, C, and D, eluted from the Sepharose™-12 gel column. The relative size of the peaks that eluted varied with different antigen preparations, but four peaks consistently eluted. Peak A eluted with the void volume (molecular weight greater than $2 \times 10^6$ Da). Peak B generally eluted approximately 1.5 ml after the first peak. The shape and position of peaks C and D were more variable. ELISA activity against anti-Mi-2 serum was detected consistently in peak A, and in some runs all activity eluted in this peak. In other runs, however, activity eluted in all peaks.

Eluted fractions from peaks A, B, and D and unfractionated immunoaffinity purified antigen were analyzed on an SDS-10% polyacrylamide gel and stained with silver stain. The SDS-PAGE gels of fractions from individual peaks showed partial segregation of the different molecular weight bands that were seen in the whole affinity purified antigen. Peak A always contained bands with molecular weights 250, 240, 145, and 40 kDa. Peak B contained the 94 kDa band, and sometimes 250, 240, 145, and 40 kDa bands were also seen. Peak C contained small amounts of bands with molecular weights 94, 65, and 40 kDa. Peak D contained the 65 kDa band and sometimes a small amount of the 40 kDa band.

The affinity-purified Mi-2 bovine antigen was also applied to a MonoQ™ HR 5/5 anion exchange column (Pharmacia, Piscataway, N.J.), which had been equilibrated in 10 mM phosphate buffer, pH 7.0, and then washed extensively with the same buffer. The column was eluted with a linear gradient of 0–1000 mM NaCl in 10 mM phosphate buffer, pH 7.0. Fractions were collected and either tested for antigenic activity by ELISA with known anti-Mi-2 sera as controls, or analyzed on SDS-PAGE.

The elution profile from the Mono-Q FPLC column showed a large number of small peaks over a broad elution range, but the larger peaks between 0.38 and 0.48 M NaCl contained activity as measured by ELISA. Maximum activity eluted in the peak at 0.43 M NaCl. SDS-PAGE of the eluted fractions demonstrated partial separation of the bands found in whole affinity antigen. The 65 kDa band was seen in fractions that eluted between 0.2–0.35 M NaCl. The 250, 240, 145 and 40 kDa bands eluted in fractions from 0.4 to 0.45 M NaCl. In the fraction that eluted at 0.45–0.47 M NaCl, the 94 kDa band and an additional band of 85 kDa were eluted and were visible on SDS-PAGE. There was also a small amount of the 40 kDa band in this fraction. SDS-PAGE of the other fractions did not show any visible bands.

EXAMPLE 5

Cloning of DNA that Encodes the Human Mi-2 Antigen

A human thymocyte lambda $gt_{11}$ expression library (Clontech Laboratories, Inc., Palo Alto, Calif.) was expressed in *E. coli* Y1090 and was screened with serum from a dermatomyositis patient. This serum had previously been tested by immunoprecipitation and by the Ouchterlony method, using bovine thymus nuclear extracts, for the presence of autoantibodies. The only autoantibodies that it contained were anti-Mi-2 autoantibodies.

Two cDNA clones, L1 and L2, were selected that expressed protein that reacted with the anti-Mi-2 serum, but that did not react with serum from normal controls or with serum obtained from a dermatomyositis patient containing autoantibodies other than anti-Mi-2.

A second lambda $gt_{11}$ expression library, a HeLa library, was similarly screened and two clones, L3 and L4, were selected which also reacted specifically with anti-Mi-2 serum.

Clone L1 was then used to screen sera from 40 patients. These sera had previously been shown to be positive for the anti-Mi-2 autoantibody. All of the 40 samples were Mi-2 positive. Control myositis patients and normals were all negative.

Each of the four clones were then characterized. The cloned DNA was expressed and blotted onto nitrocellulose. Serum containing the anti-Mi-2 antibody was then reacted with nitrocellulose from one of the clones. The bound antibody was eluted and reacted with the nitrocellulose strips on which the other clones had been blotted. Each of the other three clones reacted similarly with the eluted antibody, which indicates that each of the clones encodes the same epitope(s). In view of the similar reactivity and size (each of the inserts was 1.1 kB), the four clones are most likely identical.

The insert from one of these clones, designated clone L1, was completely sequenced. The nucleotide sequence of clone L1 is set forth below as Sequence Listing ID No. 1. The corresponding amino acid sequence is set forth below as Sequence Listing ID No. 2.

Nucleotide Seauence of Clone L1 of Human Mi-2
(Sequence Listing ID No. 1)

GAA TTC CGG CTA GGG CTT CTG GGT GGC AAG
AGG AAG AAA GGA GGC TCG AGC GAC GAA GGT
CCT GAA CCA GAG GCT GAG GAA TCA GAC CTG
GAC AGT GGC AGT GTC CAC AGT GCC TCA GGC
CGG CCT GAT GGC CCT GTC CGC ACC AAG AAA
CTA AAG AGA GGC CGG CCA GGA AGG AAG AAG
AAG AAG GTC CTG GGC TGT CCT GCA GTG GCC
GGG GAG GAG GAG GTT GAT GGC TAC GAG ACG
GAT CAC CAG GAT TAC TGT GAG GTG TGC CAG
CAG GGT GGG GAA ATT ATT CTG TGT GAC ACC TGC
CCT CGT GCC TAC CAC CTC GTC TGC CTT GAT CCT
GAG CTT GAC CGG GCT CCA GAG GGC AAA TGG
AGC TGC CCT CAC TGT GAG AAG GAG GGG GTC
CAG TGG GAG GCC AAG GAG GAA GAA GAA GAA
TAC GAA GAG GAG GGA GAG GAA GAA GGG GAG
AAG GAG GAG GAG GAT GAT CAC ATG GAG TAC
TGC CGC GTA TGC AAG GAC GGC GGG GAG CTC
CTG TGC TGT GAC GCG TGC ATC TCC TCC TAC CAC
ATT CAT TGT CTA AAC CCT CCC CTG CCT GAC ATT
CCC AAT GGT GAA TGG CTG TGT CCC CGA TGC ACA
TGC CCC GTG CTG AAG GGT CGA GTG CAG AAG
ATC CTA CAT TGG CGG TGG GGG GAG CCA CCT GTA
GCA GTG CCA GCC CCT CAA CAG GCA GAT GGA
AAT CCA GAT GTC CCA CCC CCC CGT CCT CTT CAA
GGC AGA TCA GAG CGA GAG TTC TTT GTC AAG
TGG GTA GGA CTA TCC TAC TGG CAC TGC TCC TGG
GCC AAG GAG CTT CAG CTG GAA ATC TTC CAT TTG
GTT ATG TAT CGA AAC TAC CAG CGG AAG AAT GAC
ATG GAT GAG CCC CCA CCC CTG GAC TAT GGC TCC
GGC GAG GAT GAT GGG AAG AGC GAC AAG CGT
AAA GTG AAA GAC CCG CAC TAT GCT GAG ATG
GAG GAG AAG TAC TAT CGT TTT GGC ATC AAG CCA
GAG TGG ATG ACC GTC CAC CGC ATC ATC AAC CAC
AGT GTG GAT AAA AAG GCC GGA ATT

Amino Acid Sequence of Clone L1 of Human Mi-2
(Sequence Listing ID No. 2)

Glu Phe Arg Leu Gly Leu Leu Gly Gly Lys Arg Lys Lys Gly
Gly Ser Ser Asp Glu Gly Pro Glu Pro Glu Ala Glu Glu Ser
Asp Leu Asp Ser Gly Ser Val His Ser Ala Ser Gly Arg Pro
Asp Gly Pro Val Arg Thr Lys Lys Leu Lys Arg Gly Arg Pro
Gly Arg Lys Lys Lys Val Leu Gly Cys Pro Ala Val Ala
Gly Glu Glu Glu Val Asp Gly Tyr Glu Thr Asp His Gln Asp
Tyr Cys Glu Val Cys Gln Gln Gly Gly Glu Ile Ile Leu Cys
Asp Thr Cys Pro Arg Ala Tyr His Leu Val Cys Leu Asp Pro
Glu Leu Asp Arg Ala Pro Glu Gly Lys Trp Ser Cys Pro His
Cys Glu Lys Glu Gly Val Gln Trp Glu Ala Lys Glu Glu Glu
Glu Glu Tyr Glu Glu Glu Gly Glu Glu Glu Gly Glu Lys Glu
Glu Glu Asp Asp His Met Glu Tyr Cys Arg Val Cys Lys Asp
Gly Gly Glu Leu Leu Cys Cys Asp Ala Cys Ile Ser Ser Tyr
His Ile His Cys Leu Asn Pro Pro Leu Pro Asp Ile Pro Asn
Gly Glu Trp Leu Cys Pro Arg Cys Thr Cys Pro Val Leu Lys
Gly Arg Val Gln Lys Ile Leu His Trp Arg Trp Gly Glu Pro
Pro Val Ala Val Pro Ala Pro Gln Gln Ala Asp Gly Asn Pro
Asp Val Pro Pro Arg Pro Leu Gln Gly Arg Ser Glu Arg
Glu Phe Phe Val Lys Trp Val Gly Leu Ser Tyr Trp His Cys
Ser Trp Ala Lys Glu Leu Gln Leu Glu Ile Phe His Leu Val
Met Tyr Arg Asn Tyr Gln Arg Lys Asn Asp Met Asp Glu Pro
Pro Pro Leu Asp Tyr Gly Ser Gly Glu Asp Asp Gly Lys Ser
Asp Lys Arg Lys Val Lys Asp Pro His Tyr Ala Glu Met Glu

Glu Lys Tyr Tyr Arg Phe Gly Ile Lys Pro Glu Trp Met Thr Val His Arg Ile Ile Asn His Ser Val Asp Lys Lys Ala Gly Ile

The sequences set forth in Sequence Listing ID Nos. 1 and 2 encode at least one epitope of the human Mi-2 antigen. The 1.1 kB insert includes a single long open reading frame that spans the entire insert, in phase with the beta-galactosidase. Other reading frames are either to small to encode a conformational epitope or not in phase with beta-galactosidase. Because there are no start or stop codons, the 1.1 kB insert does not include the entire gene.

An analysis of the animo acid and codon frequency of the cloned human Mi-2 fragment designated L1 is set forth in Table 2.

TABLE 2

Amino acid and codon frequency analysis of the cloned human Mi-2 fragment

| amino acid | Codon and number | | | | | | total | % |
|---|---|---|---|---|---|---|---|---|
| Ala | (GCT)3 | (GCC)7 | (GCA)3 | (GCG)1 | | | 14 | 3.99 |
| Arg | (CGT)4 | (CGC)3 | (CGA)4 | (CGG)6 | (AGA)2 | (AGG)2 | 21 | 5.98 |
| Asn | (AAT)3 | (AAC)3 | | | | | 6 | 1.71 |
| Asp | (GAT)13 | (GAC)12 | | | | | 25 | 7.12 |
| Cys | (TGT)7 | (TGC)11 | | | | | 18 | 5.13 |
| Gln | (CAA)2 | (CAG)8 | | | | | 10 | 2.85 |
| Glu | (GAA)14 | (GAG)32 | | | | | 46 | 13.11 |
| Gly | (GGT)5 | (GGC)14 | (GGA)6 | (GGG)8 | | | 33 | 9.40 |
| His | (CAT)3 | (CAC)10 | | | | | 13 | 3.70 |
| Ile | (ATT)5 | (ATC)6 | (ATA)0 | | | | 11 | 3.13 |
| Leu | (TTA)0 | (TTG)1 | (CTT)5 | (CTC)2 | (CTA)5 | (CTG)10 | 23 | 6.55 |
| Lys | (AAA)6 | (AAG)22 | | | | | 28 | 7.98 |
| Met | (ATG)5 | | | | | | 5 | 1.42 |
| Phe | (TTT)2 | (TTC)3 | | | | | 5 | 1.42 |
| Pro | (CCT)12 | (CCC)8 | (CCA)9 | (CCG)1 | | | 30 | 8.55 |
| Ser | (TCT)0 | (TCC)5 | (TCA)3 | (TCG)1 | (AGT)4 | (AGG)3 | 16 | 4.56 |
| Thr | (ACT)0 | (ACC)3 | (ACA)1 | (ACG)1 | | | 5 | 1.42 |
| Trp | (TGG)9 | | | | | | 9 | 2.56 |
| Tyr | (TAT)4 | (TAC)9 | | | | | 13 | 3.70 |
| Val | (GTT)2 | (GTC)8 | (GTA)3 | (GTG)7 | | | 20 | 5.70 |
| STOP | (TAA)0 | (TAG)0 | (TGA)0 | | | | | | molecular weight = 39973
number of amino acids = 351
Arg + Lys = 49
Asp + Glu = 71

EXAMPLE 6

Sequence Analysis of the 100 kDa Component of the Human PM-Scl Antigen

The full-length cDNA sequence coding for the 100 kDa component of the human PM-Scl antigen, the most commonly antigenic protein of the PM-Scl complex, was determined as follows.

Samples of sera from patients suffering from polymyositis-scleroderma overlap were tested for reactivity with Western blots of HeLa cell extract. The sera had been shown to contain the anti-PM-Scl antibody by immunoprecipitation and immunodiffusion against bovine thymus nuclear extracts.

HeLa cell extract was prepared as described in Example 1. The Western blots were prepared as described in Example 5. Sera from 39 patients were found to contain anti-PM-Scl by immunodiffusion and confirmed by immunoprecipitation. Each positive serum was tested by immunoblotting against whole HeLa cell extract to determine the antigenic proteins for each serum Twenty-three sera (59%) stained a 100 kD band; 16 sera (41%) stained the 100 kD band and a 70 kD band (Tables 3 and 4); one serum stained the 70 kD band without staining the 100 kD band; two sera stained bands of 30 and 32 kD; three sera stained a band of approximately 50 kD; ten sera weakly stained a band of 85 kD, including seven with both 100 kD and 70 kD reactivity, one with only 70 kD reactivity, and one that was negative for all other bands; some sera stained a 95 kD band that appeared to be a degradation product of the 100 kD band. Other bands were unique to individual sera. Nine sera had negative immunoblots.

Isolation of Pm-Scl cDNA Clone

Serum from patient JH, a patient with diffuse scleroderma, shown to contain anti-PM-Scl by immunodiffusion and containing antibody to PM-Scl, was used to screen a human thymocyte cDNA lambda $gt_{11}$ expression library from Clontech Laboratories (Palo Alto, Calif.) and a similar Clontech library prepared from HeLa cells. Serum from patient JH was diluted 1/500 in TBST (0.05 M Tris buffer at pH 8.0 with 0.15 M NaCl and 0.05% Tween™-20 surfactant), with 2% bovine serum albumin and 10 mM sodium azide. 25,000 plaque-forming units (pfu) of recombinant bacteriophage per 150 mm Petri dish were plated with *E. coli* strain Y1090 cells on LB agar. The plates were incubated at 42° C. for 3–4 hours, overlayered with nitrocellulose membranes soaked in isopropyl-thio-beta-galactoside (IPTG), and incubated for another three hours at 37° C. The membranes were then washed, incubated with diluted patient serum, and developed as for immunoblotting, using alkaline-phosphatase-coupled anti-human IgG conjugate and 5-bromo-4-chloro-3-indolyl phosphate/nitro blue tetrazolium (BCIP/NBT) substrate.

In immunoblotting against whole HeLa cell extract, serum JH serum reacted with both the 100 and 70 kD proteins, and also other bands. Screening of $2 \times 10^6$ recombinants with serum JH yielded two lambda $gt_{11}$ clones from the thymocyte library that persistently produced immunoreactive plaques. The two clones, designated $JH4B_1$ and JH4C$_1$, were plaque-purified. No clones were identified from the HeLa cell library after the screening of 2×10$^6$ recombinants.

Sera from 33 of 39 patients that had been previously found to be positive for anti-PM-Scl by immunodiffusion reacted with clone JH4B$_1$ plaques (84.6%), while 37 of 39 (94.9%) reacted with clone JH4C$_1$ plaques, of which 26 (66.7%) stained strongly at 3–4+. The 4 sera that did not stain JH4B$_1$ plaques but did stain JH4C$_1$ plaques generally stained JH4C$_1$ weakly (1+), suggesting that the difference in reactivity between the clones was quantitative rather than qualitative. As shown in Tables 3 and 4, 22 of 23 sera with anti-100 kD activity in immunoblotting were positive against plaques of both clones, and the other reacted faintly with JH4C$_1$. The serum with anti-70 kD activity but not anti-100 kD also reacted with both clones. Four of six sera reacting only with other bands in immunoblotting (neither 100 kD nor 70 kD) reacted with both clones, while the other two reacted with neither clone, the only two sera of the 39 tested that were negative against JH4C$_1$. Six of nine sera that were negative in immunoblot reacted with both clones, and the other three reacted weakly with JH4C$_1$. Reactivity with JH4B$_1$ plaques was statistically associated with anti-100 kD activity (p=0.03 by Fisher's exact test) but not anti-70 kD activity (p=0.12). None of the sera from twenty patients with other autoantibodies, nor sera from six normal controls reacted with plaques of either clone.

To confirm that this reactivity was with fusion protein, three sera were further tested in immunoblotting. Reaction against a lysate of *E. coli* produced by the JH4C$_1$ lambda gt$_{11}$ bacteriophage clone was compared to reaction with a lysate produced by wild type lambda gt$_{11}$. A protein of approximately 200 kD was recognized by all three anti-PM-Scl sera in JH4C$_1$ lysate, but was not found in wild type lysate. The two normal sera did not recognize any proteins in this region from either lysate. Thus, proteins carrying antigenic determinants recognized specifically by most anti-PM-Scl sera were expressed by these clones, suggesting that the inserts coded for some or all of an antigenic protein, or epitope, of the PM-Scl complex.

TABLE 3

COMPARISON OF IMMUNOBLOT TO REACTION WITH JH4 ANTI-PM-Scl CLONES FOR ANTI-PM-Scl SERA

| Serum # | 100 kD | 70 kD | Other | JH4B$_1$ | JH4C$_1$ |
|---|---|---|---|---|---|
| 1 | + | + | + | 4+ | 4+ |
| 2 | + | + | + | 3+ | 3+ |
| 3 | + | + | − | 3+ | 4+ |
| 4 | + | + | − | 3+ | 3+ |
| 5 | + | + | − | 4+ | 3+ |
| 6 | + | + | + | 2+ | 3+ |
| 7 | + | + | + | 3+ | 3+ |
| 8 | + | + | − | 4+ | 3+ |
| 9 | + | + | + | 4+ | 4+ |
| 10 | + | + | + | 4+ | 4+ |
| 11 | + | + | + | 3+ | 2+ |
| 12 | + | + | + | 3+ | 2+ |
| 13 | + | + | + | 2+ | 3+ |
| 14 | + | + | + | 2+ | 3+ |
| 15 | + | + | + | 2+ | 2+ |
| 16 | + | + | − | 4+ | 3+ |
| 17 | + | − | − | 1+ | 3+ |
| 18 | + | − | − | 4+ | 4+ |
| 19 | + | − | − | 4+ | 4+ |
| 20 | + | − | − | − | 1+ |
| 21 | + | − | + | 4+ | 4+ |
| 22 | + | − | + | 4+ | 3+ |
| 23 | + | − | + | 4+ | 4+ |
| 24 | − | + | + | 2+ | 1+ |
| 25 | − | − | + | 3+ | 2+ |
| 26 | − | − | + | 1+ | 1+ |
| 27 | − | − | + | 4+ | 3+ |
| 28 | − | − | + | − | − |
| 29 | − | − | − | − | − |
| 30 | − | − | + | 3+ | 4+ |
| 31 | − | − | − | 4+ | 3+ |
| 32 | − | − | − | 1+ | 2+ |
| 33 | − | − | − | 1+ | 2+ |
| 34 | − | − | − | 3+ | 4+ |
| 35 | − | − | − | − | 1+ |
| 36 | − | − | − | − | − |
| 37 | − | − | − | 3+ | 3+ |
| 38 | − | − | − | 1+ | 1+ |
| 39 | − | − | − | − | 2+ |

All 39 sera were positive for anti-PM-Scl by immunodiffusion, and were tested for reaction with the 100 kD and the 70 kD bands on immunoblot against whole HeLa cell extract. Reaction in immunoblot was assessed as positive (+) or negative (−), while positive reaction against the two JH4 clones was estimated as 1+ through 4+. "Other" referred to reaction in immunoblot with bands other than the 100 kD and 70 kD bands.

TABLE 4

SUMMARY OF REACTIONS OF ANTI-PM-Scl SERA

| | | CLONE JHRC$_1$ | |
|---|---|---|---|
| WB-100 kD | WB-70 kD | + (%) | − (%) |
| + | + | 16 (41) | 0 (0) |
| + | − | 7 (18) | 0 (0) |
| − | + | 1 (2.6) | 0 (0) |
| − | − | 13 (32.5) | 2 (5.1) |

Summary of reactions of all 39 sera found to be positive for anti-PM-Scl in immunodiffusion as described in Table 3 above.

Confirmation of the Identity of the Clones

The immunological specificity of the expressed protein of the two clones was confirmed by testing affinity purified antibody reactive with the plaques. Affinity-purified antibody eluted from plaque proteins of both JH4 clones after incubation of the plaques with JH serum (JH4 eluates), was compared to antibody eluted from plaque proteins of IPTG-induced wild-type lambda gt$_{11}$ after incubation of the plaques with JH serum (wild-type eluates). Eluates of either JH4 clone showed strong activity against plaques of both the JH4B$_1$ and JH4C$_1$ clones, demonstrating that the affinity purified antibody remained immunologically active, and also that the expressed proteins of the two clones shared antigenic determinants. Wild-type eluates were negative against the plaques of both clones. Background seen with wild-type eluates initially disappeared when the JH serum used for incubation had been pre-absorbed with wild-type plaque proteins to reduce anti-*E. coli* antibodies.

JH4 eluates were found to stain the nucleoli of HEp-2 cells, in a pattern similar to that expected with anti-PM-Scl and seen with whole JH serum. In contrast, wild-type eluates were negative in immunofluorescence. JH4B$_1$ eluate stained a 100 kD protein in immunoblotting against whole HeLa cell extract, similar in size to the 100 kD protein stained by whole JH serum. However, the 70 kD protein and other proteins stained in immunoblotting by whole JH serum were not seen with affinity-purified antibody. Wild-type eluates were negative in immunoblotting. JH4B$_1$ eluate also was active in $^{35}$S-immunoprecipitation, showing the 100 kD band along with the typical bands smaller than 40 kD in a pattern similar to that seen with whole JH serum. The immunoprecipitation of the full complex is expected in this technique, despite the fact that affinity purified antibodies reactive with only a single component were used. Wild-type eluate also showed this pattern, but it was faint, and much weaker than that seen with JH4B. eluate. These studies indicated that anti-100 kD anti-PM-Scl antibodies reacted with the protein expressed by the JH4 clones.

Sequencing of PM-Scl cDNA

The DNA of clones JH4B$_1$ and JH4C$_1$ were digested with EcoRI. Agarose gel electrophoresis of the products showed a similar sized single insert of approximately 2.5 kb for each clone. Inserts from both clones were subcloned into the poly-linker region of pUC18. Partial sequencing from the double-stranded plasmid DNA showed that both clones had identical terminal sequences.

Figure 3:
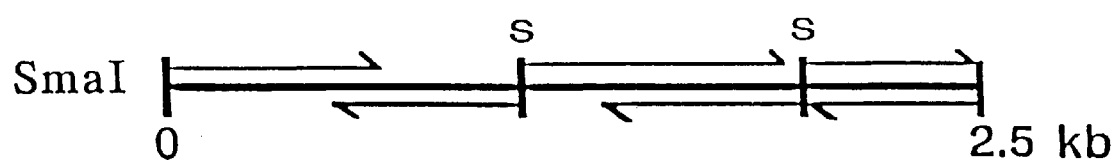
FIG. 3 is the sequence strategy for fragments obtained by digestion with SmaI. The arrows show the maximum sequenced length and direction for each fragment.
Figure 4:
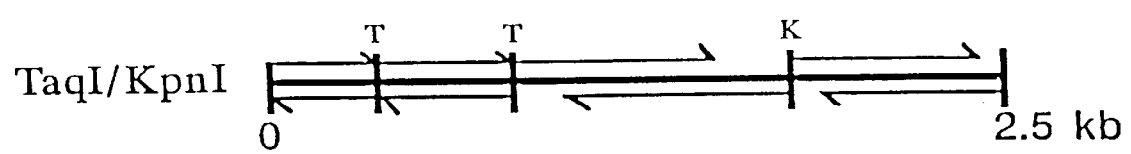
FIG. 4 is the sequence strategy for fragments obtained by digestion with KpnI and TaqI. The arrows show the maximum sequenced length and direction for each fragment.

A restriction map of the JH4B$_1$ insert was obtained by single and double digestions with selected restriction enzymes as shown in FIG. 2. Three fragments were obtained following SmaI digestion as shown in FIG. 3 and four fragments were obtained by digestion with KpnI and TaqI as shown in FIG. 4. Sequencing experiments on all fragments were performed several times. This strategy resulted in sequencing of the full length of each strand. All seven fragments of JH4B. were then isolated from agarose gels, and both strands were subcloned into the Ml3mpl8 vector and sequenced using the dideoxynucleotide chain-termination method of Sanger et al., *Proc. Natl. Acad. Sci. USA* 74:5463–5467 (1977), using $^{35}$S-labeled dATP and T7 DNA polymerase (either from United States Biochemical [Sequenase Version 2.0] or Pharmacia LKB Biotechnology, Piscataway, N.J.) by the method of Tabor and Richardson, *Proc. Natl. Acad. Sci. USA* 84:4767–4771 (1987). Compression regions were resolved by using dITP. Subclones from each of these strategies were used to verify the positions of the five restriction sites shown in FIG. 2.

The DNA sequence of both strands of the JH4B$_1$ insert, plus the 5' and 3' ends of the insert, determined as described below, was thus determined and is set forth herein as Sequence Listing ID No. 3. The corresponding amino acid sequence is set forth herein as Sequence Listing ID No. 4.

Nucleotide Sequence of 100 kDa Component of
Human PM-Scl (Sequence Listing ID No. 3)
GACAAGCTCTCGCGAGACGAGCCGTG-
CAGGCTGAAAAAATGGCGCCACCCAG-
TACCCGGGAGCCC AGGGTCCTGTCGGCGAC-
CAGCGCAACCAAATCCGACGGAGAGATGGTGCT
GCCAGGCTTCCCGGA CGCCGACAGCTTTGT-
GAAGTTTGCTCTTGGGTCCGTGGTG-
GCAGTCACCAAGGCATCTGGGGCC TACCA-
CAGTTTGGCGATGAGTATGATTTTTACCGAAGTTT
TCCTGGCTTCCAAGCATTTTGCGAA ACACAGG-
GAGACAGGTTGCTTCAGTGCATGAGCA-
GAGTAATGCAGTACCATGGGTGTCGCAGCAA CAT-
TAAGGATCGAAGTAAAGTGACTGAGCTGGAAGACA
AGTTTGATTTACTAGTTGATGCCAATG ATGTAAT-
TCTGGAGAGAGTGGGTATTTTACTGGAT-
GAAGCCTCAGGTGTAAACAAGAATCAACAG CCT-
GTCCTCCCTGCCGGCTTGCAGGTCCCCAAAACGGTA
GTGTCCAGCTGGAACCGTAAGGCAGC AGAATATG-
GCAAAAAAGCAAAATCTGAAACTTTCCG-
GCTGCTTCATG-
CAAAAAATATCATCCGAC CTCAGCTCAAGTTTC-
GAGAGAAGATTGACAATTCCAACACACCATTTCTTC
CTAAAATCTTCATC AAACCCAATGCTCAGAAAC-
CTCTCCCTCAAGCTCTCTAAGGAAAG-
GCGGGAACGCCCACAGGA TCGTCCTGAGGACTTG-
GACGTCCCCCCTGCACTGGCTGATTTCATCCATCAG
CAGAGAACCCAGC AGGTTGAGCAAGACATGTTTG-
CACATCCTTATCAATATGAACTAAAT-
CACTTTACCCCAGCAGAT GCAGTGCTTCAAAAGC-
CACAACCCCAGTTATACAGACCTATAGAAGAGACA
CCATGCCATTTCAT ATCCTCCCTGGAT-
GAACTCGTGGAACTCAACGAAAAGCTCT-
TGAATTGTCAGGAATTTGCAGTTG ACTTGGAG-
CACCACTCTTACAGGAGCTTCCTGGGACTGACCTG
CCTGATGCAAA TTTCTACTCGG ACGGAAGACT-
TCATCATTGACACCCTCGAGCTTC-
GAAGTGACATGTACATTCTCAATGAGAGCCT
CACAGACCCAGCCATCGTTAAG-
GTCTTTCATGGTGCTGATTCAGACATA-
GAATGGCTACAGAAAG ACTTTGGGTTGTATGTAG-
TAAACATGTTTGATACTCATCAGGCAGCACGCCTTC
TTAACCTGGGC AGGCACTCACTCGATCATCTCCT-
GAAACTCTACTGCAACGTGGACTCAAA-
CAAGCAATATCAGCT GGCTGATTGGAGAATACGC-
CCTCTGCCCGAGGAGATGCTCAGCTACGCCCGGGA
TGACACCCATT ACCTGCTATATATCTATGACAAAT-
GAGGCTGGAGATGTGGGAGCGCG-
GCAACGGGCAGCCCGTGC AGCTGCAGGTGGTGTG-
GCAACGGAGCAGGGACATCTGCCTCAAGAAATTCA
TCAAACCTATCTTC ACGGATGAGTCCTACCT-
TGAACTCTATAGGAAGCAGAAGAAGCAC-
CTTAACACACAGCAGTTGAC AGCCTTTCAGCTGCT-
GTTTGCCTGGAGGGATAAAACAGCTCGCAGGGAAG
ATGAAAGTTACGGAT ATGTACTGCCAAACCACAT-
GATGCTGAAAATAGCTGAAGAACTGC-
CTAAGGAACCTCAGGGCATC ATAGCTTGCTG-
CAACCCAGTACCGCCCCTTGTGCGGCAGCAGATCA
ACGAAATGCACCTTTTAAT CCAGCAGGC-
CCGAGAGATGCCCCTGCTCAAGTCT-
GAAGTTGCAGCCGGAGTGAAGAAGAGCGGAC
CGCTGCCCAGTGCTGAGAGATTG-
GAGAATGTTCTCTTTGGACCTCACGACT-
GCTCCCATGCCCCT CCGGATGGCTATCCAATCATC-
CCAACCAGTGGATCTGTGCCAGTTCAGAAGCAGGC
GAGCCTCTT CCCTGATGAAAAAGAAGATAACT-
TGCTGGGTACCACATGCCTGATTGCCA-
CAGCTGTCATCACGT TATTTAATGAACCTAGTGCT-
GAAGACAGTAAAAAGGGTCCATTGACAGTTGCACA
GAAAAAAGCC CAGAACATCATGGAGTC-
CTTTGAAAATCCATTTAGGATGATCAG-
CAACCGTTGGAAGCTGGCCCA GGTACAAGTA-
CAAAAAGAGACTAAAGAAGCTGTCAAGAAGAAGG
CAGCTGAGCAAACAGCTGCCC GGGAACAG-
GCAAAGGAGGCGTGCAAAGCTGCAGCA-
GAACAGGCCATCTCCGTCCGACAGCAGGTC
GTGCTAGAAAATGCTGCAAAGAA-
GAGAGAGCGAGCAACAAGCGACCCAAG-
GACCACAGAACAGAA ACAAGAGAAGAAACGACT-
CAAAATTTCCAAGAAGCCAAAGGACCCAGAGCCA
CCAGAAAAAGAGT TTACGCCTTACGACTACAGC-
CAGTCAGACTTCAAGGCTTTTGCTG-
GAAACAGCAAATCCAAAGTT TCTTCT-
CAGTTTGATCCAAATAAACAGACCCCGTCTGGCAA
GAAATGCATTGCAGCCAAAAAAAT TAAACAGTCG-
GTGGGAAACAAAAGCATGTCCTTTC-
CAACTGGAAAGTCAGACAGAGGCTTCAGGT
ACAACTGGCCACAGAGATAGTCCTGGAA-
GACACGTGGCGCCTGTGGACCGGAAG-
CACCAAATGCT GGTGCTGCTTTTGTACATA-
CATATTTTTAAACCATTAAAATTCTTCCTGAAGAAA
AAAAAAAAAA AAAAAAAA Amino Acid Sequence of 100 kDa Component of Human PM-Scl (Sequence Listing ID No. 4)

MetAlaProProSerThrArgGlu-
ProArgValLeuSerAlaThrSerAlaThrLysSerAsp GlyGlu-
MetValLeuProGlyPheProAspAl-
aAspSerPheValLysPheAlaLeuGlySer
ValValAlaValThrLysAlaSerGlyG-
lyLeuProGlnPheGlyAspGluTyrAspPheTyr ArgSerPhePro-
GlyPheGlnAlaPheCysGluThrGlnG-
lyAspArgLeuLeuGlnCysMet
SerArgvalMetGlnTyrHisGly-
CysArgSerAsnIleLysAspArgserLysvalThrGlu LeuGluAs-
pLysPheAspLeuLeuValAspAlaAs-
nAspValIleLeuGluArgvalGlyIle
LeuLeuAspGluAlaSerGlyV-
alAsnLysAsnGlnGlnProValLeuProAlaGlyLeuGln Val-
ProLysThrValValSerSerTrpAs-
nArgLysAlaAlaGluTyrGlyLysLysAlaLys
SerGluThrPheArgLeuLeuHisAla-
LysAsnIleIleArgProGlnLeuLysPheArgGlu
LysIleAspAsnSerAsnThrProPh-
eLeuProLysIlePheIleLysProAsnAlaGlnLys ProLeuPro-
GlnAlaLeuSerLysGluArgArgGlu-
ArgProGlnAspArgProGluAspLeu
AspValProProAlaLeuAlaAsp-
PheIleHisGlnGlnArgThrGlnGlnValGluGlnAsp MetPheAla-
HisProTyrGlnTyrGluLeuAsnHis-
PheThrProAlaAspAlaValLeuGln
LysProGlnProGlnLeuTyrArgProI-
leGluGluThrProCysHisPheIleSerSerLeu AspGluLeuValG-
luLeuAsnGluLysLeuLeuAsnCys-
GlnGluPheAlaValAspLeuGlu
HisHisSerTyrArgserPheLeuG-
lyLeuThrCysLeuMetGlnIleSerThrArgThrGlu Asp-
PheIleIleAspThrLeuGluLeuArg-
SerAspMetTyrIleLeuAsnGluSerLeuThr
AspProAlaIleValLysvalPheHisG-
lyAlaAspSerAspIleGluTrpLeuGlnLysAsp PheGlyLeuTyr-
ValValAsnrdetPheAspThrHis-
GlnAlaAlaArgLeuLeuAsnLeuGly
ArgHisSerLeuAspHisLeuLeu-
LysLeuTryCysAsnValAspSerAsnLysGlnTyrGln LeuA-
laAspTrpArgIleArgProLeuPro-
GluGluMetLeuSerTyrAlaArgAspAspThr
HisTyrLeuLeuTyrIleTyrAspLys-
MetArgLeuGluMetTrpGluArgGlyAsnGlyGln ProValGln-
LeuGlnValValTrpGlnArgSerAr-
gAspIleCysLeuLysLysPheIleLys
ProIlePheThrAspGluSerTyrLeuG-
luLeuTyrArgLysGlnLysLysHisLeuAsnThr GlnGln-
LeuThrAlaPheGlnLeuLeuPheAla-
TrpArgAspLysThrAlaArgArgGluAsp
GluSerTyrGlyTyrValLeuProAsn-
HisMetMetLeuLysIleAlaGluGluLeuProLys GluProGlnGly-
IleIleAlaCysCysAsnProValProProLeuValArgGlnGlnIleAsn
GluMetHisLeuLeuIleGlnGlnA-
laArgGluMetProLeuLeuLysSerGluValAlaAla Gly-
ValLysLysSerGlyProLeuProSer-
AlaGluArgLeuGluAsnValLeuPheGlyPro
HisAspCysSerHisAlaProProAspG-
lyTyrProIleIleProThrSerGlySerValPro ValGlnLysGlnAla-
SerLeuPheProAspGluLysGlu-
AspAsnLeuLeuGlyThrThrCys
LeuIleAlaThrAlaValIleThrLe-
uPheAsnGluProSerAlaGluAspSerLysLysGly ProLeuThrV-
alAlaGlnLysLysAlaGlnAs-
nIleMetGluSerPheGluAsnProPheArg MetIleSerAsnArgTrpLysLeuAla-
GlnValGlnValGlnLysAspSerLysGluAlaVal LysLysLysA-
laAlaGluGlnThrAlaAlaArg-
GluGlnAlaLysGluAlaCysLysAlaAla
AlaGluGlnAlaIleSerValArg-
GlnGlnValValLeuGluAsnAlaAlaLysLysArgGlu ArgAlaTh-
rSerAspProArgThrThrGluGlnLys-
GlnGluLysLysArgLeuLysIleSer
LysLysProLysAspProGluProProG-
luLysGluPheThrProTyrAspTyrSerGlnSer AspPheLysAl-
aPheAlaGlyAsnSerLysSerLys-
ValSerSerGlnPheAspProAsnLys
GlnThrProSerGlyLysLysCysIleA-
laAlaLysLysIleLysGlnSerValGlyAsnLys SerMetSerPhePro-
ThrGlyLysSerAspArgGlyPheArgTyrAsnTrpProGlnArg Including EcoRI linkers (not indicated), the JH4B$_1$ insert contained 2477 nucleotides, with a single long open reading frame of 2303 nucleotides from the first ATGcodon at position 288, to a stop codon at position 2619. The predicted protein from the insert cDNA included 777 amino acids, with a predicted molecular mass of 89 kD, smaller than the observed mass of the antigenic protein in this example (100 kD) or that reported in other studies (110 kD). This would not necessarily exclude the possibility that this was the full-length CDNA, since the predicted size by amino acid sequence of some proteins, including the PM-Scl 75 kD protein, is smaller than the relative mass observed in SDS-PAGE, either because of unusual charge patterns or post-translational modification. No poly-(A) tail was seen in the cDNA insert.

Northern Blot Analysis

Northern blot against total RNA and poly-(A)$^+$ RNA from HeLa cells showed hybridization of $^{32}$P-labeled cDNA insert isolated from clone JH4B$_1$ with a single band of 2.7 kb, 40 µg or 20 µg of total HeLa RNA, or 8 µg of isolated poly-(A)$^+$ HeLa RNA was electrophoresed in a 1% agarose gel, transferred to Nytran™ membrane, and a hybridized with $^{32}$P-labeled PM-Scl-100 kD cDNA insert isolated from clone JH4B$_1$. A single, strong, thick band was identified in all 3 preparations in each case. Similar results showing hybridization of a single 2.7 kb band were obtained using total RNA from an SKHepl cell line from human liver adenocarcinoma. This indicated that the PM-Scl mRNA was 2.7 kb long. The isolated JH4 CDNA inserts, at less than 2.5 kb, included most but not all of the full length of the corresponding mRNA, although the extra length may have been in untranslated regions.

Determination of the 5' and 3' Ends of the cDNA Sequence

The ends of the cDNA were extended and amplified by the following procedure. Additional cDNA sequence for the gene for the PM-Scl 100 kD protein not included in the bacteriophage insert was obtained by using the methods of Loh et al., Science, 243:217–220 (1989) and Frohman et al., Proc. Natl. Acad. Sci. USA 85:8998–9002 (1988).

For amplification of the 5' end of the cDNA, 15 µg of total HeLa cell RNA and 2 µg of HeLa cell poly-(A)$^+$ RNA were separately reverse transcribed using the cDNA Cycle kit (Invitrogen, San Diego, Calif.), with a gene-specific primer of 22 nucleotides beginning 218 bp from the 5' end of the original cDNA insert (positions 410 through 431 in Sequence Listing ID No. 3). When reverse transcription was complete, 2 µl of RNAse-A (10 mg/ml) were added to the reverse transcribed CDNA pool and incubated at 37° C. for 30 minutes. Excess primer and deoxynucleotide triphosphates were removed by three rounds of spin filtration in a Centricon-30 (Amicon Division, WR Grace, Danvers, Mass.), in 5 mM Tris-HCl buffer at pH 8.0 with 0.5 mM EDTA. The sample was concentrated in a vacuum centrifuge and adjusted to 23 µl with $H_2O$. A terminal deoxynucleotidyl-transferase tailing reaction was then performed according to instructions from Promega Corporation, Madison, Wis.

The resulting extended, tailed 5' end was amplified using the polymerase chain reaction (PCR). The reaction was performed in 100 µl, containing the following in final concentrations: 1×Taq DNA polymerase buffer (Promega Corporation, Madison, Wis.); 200 µM deoxynucleotide triphosphates; 0.25 µM gene-specific primer; and 0.25 µM oligo-d(T)$_{17}$ with restriction site adapter. The gene-specific primer used for amplification began 96 bp from the 5' end of the original cDNA insert and was 26 nucleotides in length (positions 292 through 310 in Sequence Listing ID No. 3) with a BglII restriction site attached. The primer was different from that used for formation of the cDNA in order to increase the specificity for this gene. The cDNA template was denatured at 95° C. for five minutes followed by chilling on ice, was centrifuged briefly, and then 2.5 units of Taq DNA polymerase (Promega Corporation, Madison, Wis.) and two drops mineral oil were added. A total of 35 cycles were performed, consisting of 94° C. for 50 seconds, 54° C. for one minute, and 72° C. for one minute, with a final elongation step at 72° C. for five minutes.

The 3' end was amplified by a similar procedure. Total RNA and poly-(A)$^+$RNA from HeLa cells were reverse-transcribed using and oligo-d(T) primer. A gene-specific primer was used for PCR amplification, beginning 91 bp upstream of the 3' end and extending 18 nucleotides (positions 2593 through 2610 in Sequence Listing ID No. 3) with a 9-nucleotide adapter. After RNAse digestion, the deoxynucleotide triphosphates were removed by using a G-50 spin column (5 Prime—3 Prime Inc., Boulder, Colo.). The extended 3' end was amplified with PCR as above.

The 5' and 3' extended cDNA products were analyzed by electrophoresis in. To confirm that the products were specific, Southern blotting was performed, in which the gel products were electroblotted onto Hybond-N™ membrane (Amersham, Arlington Heights, Ill.), and hybridization was performed with a $^{32}$P-labelled cDNA insert as probe. Specific products were isolated from the gel by diffusion. A portion of the products were subcloned into the plasmid vector pUC18 following digestion of the 5' products with PstI and BglII, or digestion of the 3' products with XbaI and PstI. Other PCR products were subcloned into the plasmid vector PCR1000 (Invitrogen, San Diego, Calif.) according to manufacturer's instructions without previous treatment. All extended products were sequenced from a double-stranded DNA template with T7 DNA polymerase (Pharmacia LKB Biotechnology, Piscataway, N.J.) as described above. The products of 5' end amplification, showed a predominant band at ranging from 320–340 bp, whether total or poly-(A)$^+$ RNA was used for the template for cDNA formation. An electrophoretic gel of the products of the PCR amplification of the 5' extension from the clone for the PM-Scl-100 kD protein, was stained with ethidium bromide and photographed under UV light. The 5' extension was reverse transcribed using either total RNA or poly-(A)$^+$ RNA as template, and both showed the same product, A smaller band obtained using total RNA appeared to be dimers. The results contained a combination of HaeIII digested ØX 174 RF DNA and Hind-III digested lambda DNA. In some PCR amplifications using the same cDNA as template, analysis of the products showed multiple bands in addition to the predominant 340 bp band. To determine whether these other bands were specific amplification products, PCR products were electroblotted after electrophoresis onto a nylon membrane and probed with $^{32}$P-labeled JH4B$_1$ insert. Only the 340 bp band hybridized. A 450 bp band was also seen on several ethidium bromide stained gels. When the PCR products were digested with BglII and PstI, whose restriction sites were attached to the gene-specific primer and the oligo-d(T) primer respectively, PAGE showed that the 450 bp band was cut in half, while the 340 bp band was unchanged, suggesting that the 450 bp band was a combination of at least two smaller PCR products unrelated to the hybridizing 340 bp band. Repeated amplifications with the same reverse-transcribed cDNA and with newly formed cDNA extension gave similar results.

In order to identify the longest extensions present, a wide range of products were isolated from the PAGE by diffusion. Aliquots of PCR products were subcloned into pUC18 or PCR1000. Nineteen subclones were obtained and eleven were selected and sequenced from plasmid mini-preps. The sequences showed that all of the clones started from the gene-specific primer, contained the 88 bp of known sequence between the start of the primer and the 5' end of the original cDNA insert (discounting the EcoRI linker), extended 180–210 nucleotides beyond the 5' insert end, and then showed the poly-(T) expected from the tailing reaction. The first initiation codon of the maximum length extended 5' portion was at position 39, outside the original cDNA. All of the 5' extension subclones contained this codon. Therefore, all PCR-produced 5' ends gave the same putative translational starting site, which differed from that which was predicted from the initial CDNA insert by 249 nucleotides (83 amino acids). None of these subclones contained an in frame stop codon upstream of the first ATG.

Two slight discrepancies were noted among the 11 sequenced 5' extensions; 1 of 11 showed a change from a T to a C at position 96 of the 5' extension, and 1 of 11 showed a change from a G to an A at position 191. Although it is possible that these represent different alleles, their low frequency suggests that they more likely represent mutant Taq polymerase products.

Although a stop codon was present in the open reading frame of the cDNA insert (position 2619 in Sequence Listing ID No. 3), the poly-(A) tail was not present, and therefore the 3' end was amplified as well. PAGE of PCR amplification products of the 3' extensions showed a predominant band at 180 bp, but multiple other bands were identified. Southern blotting and hybridization with a $^{32}$P-labeled cDNA insert, however, showed hybridization only with the 180 bp band. An aliquot of PCR products was digested with XbaI and PstI and subcloned into pUC18 and PCR1000. Eight subclones were selected for sequencing. The sequences of all of the clones started from the gene-specific primer 99 bp upstream from the 3' end of the original CDNA insert, included the 90 bp of known sequences up to the EcoRI linker, extended 32 nucleotides further, and ended with a poly-(A) tail, that usually contained approximately 20 bp. Two of the eight sequenced 3' extensions showed an absence of the three nucleotides 2716–2718 just upstream of the poly-(A) tail. A putative polyadenylation signal, ATTAAA, was located 19 nucleotides from the poly-(A) tail within the extended region.

Analysis of the Sequence

The full-length nucleotide sequence of this PM-Scl gene including the extended 5' and 3' ends was 2739 bp long. This sequence consists of 38 nucleotides in the 5' untranslated region, 2580 bp in the predicted coding region from the first methionine codon, and 100 nucleotides from the stop codon up to the 21 nucleotide poly-(A) tail. The deduced amino acid sequence was composed of 860 residues with a predicted molecular mass of 98,088.24 daltons, very close in size to the observed relative molecular weight in PAGE (100 kD).

Computer analysis of nucleotide and amino acid sequences was performed with the Sequence Analysis Software Package of the Genetics Computer Group of the University of Wisconsin as described by Devereux et al. *Nucleic Acids Res.* 12:387–395 (1984), using a VAX 8250 computer, and also using a supercomputer through the Pittsburgh Supercomputing Facility as described by Itoh et al. *J. Clin. Invest.* 87:177–186 (1991).

Several possible sites of post-translational modification were observed. Two potential N-glycosylation sites were identified at residues 353 and 839. A number of potential phosphorylation sites were identified, including those for protein kinase C (at residues 849, 823 and 846), casein kinase II (at residues 18, 104, 292, 293, 333, 370 and 665), and tyrosine kinase (at 523). There were also amidation sites identified at residues 163 and 823. However, the presence of these sites does not necessarily indicate that post-translational modification occurs at these sites, and they are often observed in proteins that are not modified. There has been no evidence of phosphorylation of the PM-Scl 100 kD protein reported. Protein motifs were examined using a database obtained from Dr. A. Bairoch, Centre Medical Universitaire, Geneva and adapted for use on a VAX computer.

One report indicated that a number of lupus and scleroderma autoantigens showed a higher frequency than other proteins of charge runs (a long series of consecutive charged amino acids) and charge clusters (a high frequency of charged amino acids, not necessarily consecutive, within a given stretch of amino acids). Although no charge runs were observed in the PM-Scl 100 kD protein, a "mixed charge cluster" (consisting of both positive and negative residues) was found between residues 753 and 789, with 14 positive and 8 negatively charged residues among 37 amino acids, for a total of 59% charged amino acids within the cluster. Tests for charged runs and clusters in protein sequences were performed using the PORPAT program described by Brendel et al. *Proc. Natl. Acad. Sci. USA*, 88:1536–1540 (1991).

There was no significant homology with the sequence of the 75 kD PM-Scl protein, and there were no sequences of more than four consecutive amino acids shared between the two proteins. Independence of the two major PM-Scl antigenic proteins on the amino acid level is consistent with the observation noted above that they were antigenically independent, because affinity-purified JH4B$_1$ eluates stained the 100 kD protein but not the 70 kD protein. No significant homology with other eukaryotic proteins in the databanks was identified.

In conclusion, the full-length sequence for the 100 kD PM-Scl protein, the major antigenic component of the PM-Scl complex, isolated from nature, was determined, showing it to be independent of the 70–75 kD protein, and unique in the databank. 56.4% of anti-PM-Scl sera react with this protein in immunoblot, while up to 94% of anti-PM-Scl sera react with the recombinant form as fusion protein, suggesting reaction with conformational epitopes.

Modifications and variations of the myositis-specific antigens, isolated nucleic acid and amino acid sequences encoding all or a portion thereof, and methods of use thereof, will be obvious to those skilled in the art from the foregoing detailed description. Such modifications and variations are intended to come within the scope of the appended claims.

We claim:

1. An isolated human Mi-2 protein comprising all or a portion of a human Mi-2 antigen comprising the amino acid sequence set forth in SEQ ID NO:2, wherein the portion includes at least one epitope of the human Mi-2 antigen which is specifically immunoreactive with an autoantibody present in the sera of a human patient with myositis and not immunoreactive with antibody to bovine Mi-2 antigen.

2. The protein of claim 1, wherein the portion comprises SEQ ID NO: 2.

3. The protein of claim 2 wherein the portion is encoded by a nucleotide molecule comprising SEQ ID NO: 1.

4. An isolated human PM-Scl protein comprising all or a portion of a PM-Scl antigen comprising the amino acid sequence set forth in SEQ ID NO:4, wherein the portion includes at least one epitope of the antigen immunoreactive with an autoantibody present in the sera of a human patient with, myositis and not immunoreactive with antibody to bovine PM-Scl antigen.

5. The protein of claim 4, wherein the portion comprises the amino acid sequence set forth in SEQ ID NO: 4.

6. The protein of claim 4 wherein the portion is encoded by a nucleotide molecule comprising SEQ ID NO: 3.

* * * * *